(12) United States Patent
Chen et al.

(10) Patent No.: US 8,865,204 B2
(45) Date of Patent: *Oct. 21, 2014

(54) MANUFACTURE OF LOZENGE PRODUCT WITH RADIOFREQUENCY

(71) Applicant: McNEIL-PPC, Inc., Skillman, NJ (US)

(72) Inventors: Jen-Chi Chen, Morrisville, PA (US);
Harry S. Sowden, Glenside, PA (US);
Joseph R. Luber, Quakertown, PA (US);
Leo B. Kriksunov, Ithaca, NY (US);
Frank J. Bunick, Randolph, NJ (US);
Christopher E. Szymczak, Marlton, NJ (US);
Gregory E. Koll, Hillsborough, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/718,357

(22) Filed: Dec. 18, 2012

(65) Prior Publication Data

US 2013/0178501 A1 Jul. 11, 2013

Related U.S. Application Data

(63) Continuation of application No. 12/887,575, filed on Sep. 22, 2010, now Pat. No. 8,343,533.

(60) Provisional application No. 61/245,315, filed on Sep. 24, 2009, provisional application No. 61/255,582, filed on Oct. 28, 2009, provisional application No. 61/314,629, filed on Mar. 17, 2010, provisional application No. 61/358,167, filed on Jun. 24, 2010.

(51) Int. Cl.
| | |
|---|---|
| A61K 9/68 | (2006.01) |
| A61K 9/20 | (2006.01) |
| A61K 9/14 | (2006.01) |
| A61K 31/44 | (2006.01) |
| A61K 47/00 | (2006.01) |
| B30B 15/34 | (2006.01) |
| B30B 11/02 | (2006.01) |
| A61K 9/28 | (2006.01) |
| A61K 9/00 | (2006.01) |
| B30B 11/10 | (2006.01) |
| A61J 3/06 | (2006.01) |
| B29C 35/08 | (2006.01) |

(52) U.S. Cl.
CPC ............. *A61J 3/06* (2013.01); *A61K 9/2086* (2013.01); *A61K 9/2031* (2013.01); *B30B 15/34* (2013.01); *B30B 11/027* (2013.01); *A61K 9/288* (2013.01); *A61K 9/2095* (2013.01); *B29C 2035/0861* (2013.01); *A61K 9/2068* (2013.01); *A61K 9/2853* (2013.01); *A61K 9/0056* (2013.01); *B30B 11/022* (2013.01); *B30B 11/10* (2013.01); *A61K 9/0058* (2013.01)

USPC ........... 424/440; 424/464; 424/465; 424/484; 514/343; 514/356; 514/789

(58) Field of Classification Search
None
See application file for complete search history.

(56) References Cited

U.S. PATENT DOCUMENTS

| | | |
|---|---|---|
| 2,183,053 A | 12/1939 | Taylor |
| 2,887,437 A | 5/1959 | Klioze et al. |
| 3,071,470 A | 1/1963 | Bishop |
| 3,337,116 A | 8/1967 | Nowak |
| 3,670,065 A | 6/1972 | Eriksson et al. |
| 3,885,026 A | 5/1975 | Heinemann et al. |
| 4,158,411 A | 6/1979 | Hall et al. |
| 4,173,626 A | 11/1979 | Dempski et al. |
| 4,230,693 A | 10/1980 | Izzo et al. |
| 4,260,596 A | 4/1981 | Mackles |
| 4,268,238 A | 5/1981 | Marc |
| 4,268,465 A | 5/1981 | Suh et al. |
| 4,327,076 A | 4/1982 | Puglia et al. |
| 4,398,634 A | 8/1983 | McClosky |
| 4,508,740 A | 4/1985 | McSweeney |
| 4,526,525 A | 7/1985 | Oiso et al. |
| 4,590,075 A | 5/1986 | Wei et al. |
| 4,609,543 A | 9/1986 | Morris et al. |
| 4,642,903 A | 2/1987 | Davies |
| 4,684,534 A | 8/1987 | Valentine |
| 4,758,439 A | 7/1988 | Godfrey |
| 4,762,719 A | 8/1988 | Forester |
| 4,824,681 A | 4/1989 | Schobel et al. |
| 4,828,845 A | 5/1989 | Zamudio-Tena et al. |
| 4,832,956 A | 5/1989 | Gergely et al. |
| 4,851,226 A | 7/1989 | Julian et al. |
| 4,857,331 A | 8/1989 | Shaw et al. |
| 4,863,742 A | 9/1989 | Panoz et al. |

(Continued)

FOREIGN PATENT DOCUMENTS

| | | |
|---|---|---|
| CN | 1141589 A | 1/1997 |
| CN | 1498080 A | 5/2004 |

(Continued)

OTHER PUBLICATIONS

Jones, P. L. et al, "Dielectric Drying", Drying Technology, 14(5), 1996, p. 1063-1098.

(Continued)

*Primary Examiner* — Jeffrey T Palenik
(74) *Attorney, Agent, or Firm* — William E. McGowan

(57) ABSTRACT

The present invention features a process for making a lozenge product including the steps of forming a powder blend containing an amorphous carbohydrate polymer into the desired shape of the lozenge product and applying radiofrequency energy to the shape for a sufficient period of time to soften or melt said amorphous carbohydrate polymer to fuse the shape into said lozenge product.

29 Claims, 18 Drawing Sheets

(56) References Cited

U.S. PATENT DOCUMENTS

| | | |
|---|---|---|
| 4,906,478 A | 3/1990 | Valentine et al. |
| 4,979,720 A | 12/1990 | Robinson |
| 4,980,170 A | 12/1990 | Schneider et al. |
| 4,984,240 A | 1/1991 | Keren-Zvi et al. |
| 4,994,260 A | 2/1991 | Kallstrand et al. |
| 5,013,557 A | 5/1991 | Tai |
| 5,046,618 A | 9/1991 | Wood |
| 5,064,656 A | 11/1991 | Gergely et al. |
| 5,073,374 A | 12/1991 | McCarty |
| 5,075,114 A | 12/1991 | Roche |
| 5,082,436 A | 1/1992 | Choi et al. |
| 5,112,616 A | 5/1992 | McCarty |
| 5,126,151 A | 6/1992 | Bodor et al. |
| 5,134,260 A | 7/1992 | Piehler et al. |
| 5,139,407 A | 8/1992 | Kim et al. |
| 5,178,878 A | 1/1993 | Webling et al. |
| 5,215,755 A | 6/1993 | Roche et al. |
| 5,223,264 A | 6/1993 | Webling et al. |
| 5,262,171 A | 11/1993 | Login et al. |
| 5,275,822 A | 1/1994 | Valentine et al. |
| 5,286,497 A | 2/1994 | Hendrickson et al. |
| 5,304,055 A | 4/1994 | Van Lengerich et al. |
| 5,320,848 A | 6/1994 | Geyer et al. |
| 5,330,763 A | 7/1994 | Gole et al. |
| 5,464,632 A | 11/1995 | Cousin et al. |
| 5,489,436 A | 2/1996 | Hoy et al. |
| 5,501,858 A | 3/1996 | Fuisz |
| 5,501,861 A | 3/1996 | Makino et al. |
| 5,503,846 A | 4/1996 | Wehling et al. |
| 5,558,880 A | 9/1996 | Gole et al. |
| 5,558,899 A | 9/1996 | Kuzee et al. |
| 5,560,963 A | 10/1996 | Tisack |
| 5,587,172 A | 12/1996 | Cherukuri et al. |
| 5,587,179 A | 12/1996 | Gergely et al. |
| 5,607,697 A | 3/1997 | Alkire et al. |
| 5,622,719 A | 4/1997 | Myers et al. |
| 5,631,023 A | 5/1997 | Kearney et al. |
| 5,635,210 A | 6/1997 | Allen, Jr. et al. |
| 5,648,093 A | 7/1997 | Gole et al. |
| 5,653,993 A | 8/1997 | Ghanta et al. |
| 5,662,849 A | 9/1997 | Bogne et al. |
| 5,672,364 A | 9/1997 | Kato et al. |
| 5,720,974 A | 2/1998 | Makino et al. |
| 5,814,339 A | 9/1998 | Prudhoe |
| 5,886,081 A | 3/1999 | Sternowski |
| 5,912,013 A | 6/1999 | Rudnic et al. |
| 5,939,091 A | 8/1999 | Eoga et al. |
| 5,997,905 A | 12/1999 | McTeigue et al. |
| 6,024,981 A | 2/2000 | Khankarti et al. |
| 6,060,078 A | 5/2000 | Lee |
| 6,103,260 A | 8/2000 | Luber et al. |
| 6,224,905 B1 | 5/2001 | Lawrence et al. |
| 6,228,398 B1 | 5/2001 | Devane et al. |
| 6,258,381 B1 | 7/2001 | Luber et al. |
| 6,270,805 B1 | 8/2001 | Chen et al. |
| 6,277,409 B1 | 8/2001 | Luber et al. |
| 6,284,270 B1 | 9/2001 | Lagoviyer et al. |
| 6,287,596 B1 | 9/2001 | Murakami et al. |
| 6,316,026 B1 | 11/2001 | Tatara et al. |
| 6,322,819 B1 | 11/2001 | Barnside et al. |
| 6,328,994 B1 | 12/2001 | Shimizu et al. |
| 6,465,010 B1 | 10/2002 | Lagoviyer et al. |
| 6,499,984 B1 | 12/2002 | Ghebre-Sellassie et al. |
| 6,569,463 B2 | 5/2003 | Patel et al. |
| 6,589,554 B1 | 7/2003 | Mizumoto et al. |
| 6,612,826 B1 | 9/2003 | Bauer et al. |
| 6,649,888 B2 | 11/2003 | Ryan et al. |
| 6,753,009 B2 | 6/2004 | Luber et al. |
| 6,767,200 B2 | 7/2004 | Sowden et al. |
| 6,814,978 B2 | 11/2004 | Bunick et al. |
| 6,932,979 B2 | 8/2005 | Gergely |
| 7,070,825 B2 | 7/2006 | Ndife et al. |
| 7,157,100 B2 | 1/2007 | Doshi et al. |
| 8,127,516 B2 | 3/2012 | Lee et al. |
| 8,313,768 B2 | 11/2012 | Kriksunov et al. |
| 8,343,533 B2 | 1/2013 | Chen et al. |
| 2001/0033831 A1 | 10/2001 | Chow et al. |
| 2002/0012701 A1 | 1/2002 | Kolter et al. |
| 2002/0018800 A1 | 2/2002 | Pinney et al. |
| 2002/0079121 A1 | 6/2002 | Ryan et al. |
| 2002/0122822 A1 | 9/2002 | Bunick et al. |
| 2003/0021842 A1 | 1/2003 | Lagoviyer et al. |
| 2003/0068373 A1 | 4/2003 | Luber et al. |
| 2003/0161879 A1 | 8/2003 | Ohmori et al. |
| 2003/0175339 A1 | 9/2003 | Bunick et al. |
| 2003/0194442 A1 | 10/2003 | Guivarch et al. |
| 2003/0224044 A1 | 12/2003 | Weibel |
| 2003/0228368 A1 | 12/2003 | Wynn et al. |
| 2004/0115305 A1 | 6/2004 | Andersen et al. |
| 2004/0137057 A1 | 7/2004 | Sowden et al. |
| 2004/0156902 A1 | 8/2004 | Lee et al. |
| 2004/0191499 A1 | 9/2004 | Hallett et al. |
| 2005/0019407 A1 | 1/2005 | Sowden et al. |
| 2005/0138899 A1 | 6/2005 | Draisey et al. |
| 2005/0142188 A1 | 6/2005 | Gilis et al. |
| 2005/0186274 A1 | 8/2005 | Kohlrausch |
| 2006/0034927 A1 | 2/2006 | Casadevall et al. |
| 2006/0134195 A1 | 6/2006 | Fu et al. |
| 2007/0071806 A1 | 3/2007 | McCarty |
| 2007/0184111 A1 | 8/2007 | Harris et al. |
| 2007/0196477 A1 | 8/2007 | Withiam et al. |
| 2007/0281009 A1 | 12/2007 | Kamisono et al. |
| 2008/0286340 A1 | 11/2008 | Andersson et al. |
| 2009/0060983 A1 | 3/2009 | Bunick et al. |
| 2009/0092672 A1 | 4/2009 | Venkatesh et al. |
| 2009/0110716 A1 | 4/2009 | Bunick et al. |
| 2009/0110717 A1 | 4/2009 | Singh et al. |
| 2010/0016348 A1 | 1/2010 | Bunick et al. |
| 2010/0016451 A1 | 1/2010 | Bunick et al. |
| 2010/0021507 A1 | 1/2010 | Bunick et al. |
| 2011/0068511 A1 | 3/2011 | Sowden et al. |
| 2011/0070170 A1 | 3/2011 | Koll et al. |
| 2011/0070286 A1 | 3/2011 | Hugerth et al. |
| 2011/0070301 A1 | 3/2011 | Luber et al. |
| 2011/0071184 A1 | 3/2011 | Bunick et al. |
| 2011/0071185 A1 | 3/2011 | Bunick et al. |
| 2011/0318411 A1 | 12/2011 | Luber et al. |
| 2011/0319441 A1 | 12/2011 | Szymczak et al. |
| 2011/0319492 A1 | 12/2011 | Luber et al. |
| 2012/0022170 A1 | 1/2012 | Bunick et al. |

FOREIGN PATENT DOCUMENTS

| | | |
|---|---|---|
| CN | 101052373 A | 10/2007 |
| EP | 0070127 | 1/1983 |
| EP | 0192460 B1 | 8/1986 |
| EP | 0416791 A2 | 3/1991 |
| EP | 0829341 A2 | 3/1998 |
| EP | 1974724 A2 | 10/2008 |
| EP | 2308511 B1 | 12/2012 |
| GB | 772 315 | 4/1957 |
| GB | 1 097 207 | 12/1967 |
| GB | 1538280 A | 1/1979 |
| JP | 59 067006 A | 4/1984 |
| JP | 62/205009 A | 3/1986 |
| JP | 649482 B | 6/1994 |
| JP | 1999033084 A | 2/1999 |
| JP | 2010531350 | 9/2010 |
| WO | WO 91/12881 | 9/1991 |
| WO | WO 92/06679 | 4/1992 |
| WO | WO 93/13758 A1 | 7/1993 |
| WO | WO 94/06416 | 3/1994 |
| WO | WO 95/09044 A1 | 4/1995 |
| WO | WO 97/38679 A2 | 10/1997 |
| WO | WO 98/32426 A1 | 7/1998 |
| WO | WO 99/17771 | 4/1999 |
| WO | WO 99/44580 A1 | 9/1999 |
| WO | WO 00/04281 | 1/2000 |
| WO | WO 02/47607 | 6/2002 |
| WO | WO 03/059327 A1 | 7/2003 |
| WO | WO 03/061399 | 7/2003 |
| WO | WO 03/101431 A1 | 12/2003 |
| WO | WO 2004/000197 A2 | 12/2003 |
| WO | WO 2004/046296 A1 | 6/2004 |

(56) References Cited

FOREIGN PATENT DOCUMENTS

| WO | WO 2004/100857 A2 | 11/2004 |
|---|---|---|
| WO | WO 2006/018074 A1 | 2/2006 |
| WO | WO 2006/127618 | 11/2006 |
| WO | WO 2007/042153 A1 | 4/2007 |
| WO | WO 2007/125545 A2 | 11/2007 |
| WO | WO 2008/005318 A2 | 1/2008 |
| WO | WO 2008/015221 A2 | 2/2008 |
| WO | WO 2009/037319 A2 | 3/2009 |
| WO | WO 2009/080022 A1 | 7/2009 |
| WO | WO 2010/058218 A1 | 5/2010 |
| WO | WO 2012/039788 A1 | 3/2012 |

OTHER PUBLICATIONS

Guo, et al., Temperature and Moisture Dependent Dielectric Properties of Legume Flour Associated with Dielectric Heating, LWT Food Science and Technology 43, 2010, p. 193-201.
Katsuki, et al., Novel Energy-Saving Materials for Microwave Heating, Chem Mater. 2008, 20, p. 4803-4807.
Radio-Frequency Heating of Plastics, TechCommentary, vol. 4, No. 2, 1987, p. 1-4.
Jones, P. L., High Frequency Dielectric Heating in Paper Making, Drying Technology, 4(2), 1986, p. 217-244.
What is R.F. Heat Sealing?, Dielectric Sealing Service, Inc., 2007, p. 1-6.
Broadband RF Survey Instruments, ETS•Lindgren Haladay EMF Measurement, 2002, p. 1-2.
Lamp IR Infrared Heaters: Infrared Lamps for Controlled Concentrated Heating, Research Inc., p. 1-20., Sep. 20, 2010.
Callebaut, Power Quality & Utilisation Guide, Section 7: Energy Efficiency, Mar. 2007, www.leonardo-energy.org, p. 1-9.
Shukla, et al., Mouth Dissolving Tablets I: An Overview of Formulation Technology, Sci Pharm 2009, 76: p. 309-326.
Lieberman, Herbert A. et al., "Pharmaceutical Dosage Forms—Tablets", vol. 2, $2^{nd}$ Ed. pp. 213-217; 327-329, Marcel Dekker, Inc., 1990, New York and Basel.
Lachman, Leon et al., "The Theory and Practice of Industrial Pharmacy", $3^{rd}$ Ed., Chapter 11, pp. 293-345,Lea & Febiger, 1986, Philadelphia.
McConville, J. et al., "Erosion characteristics of an erodible tablet incorporated in a time-delayed capsule device," Drug Development and Industrial Pharmacy, vol. 31, No. 1, 2005, pp. 79-89, XP008108019.
USP 23 (1995) 1216, Tablet Friability, p. 1981.
USP 24, 2000 Version, Acetaminophen, pp. 19-20 and Ibuprofen, p. 856 (1999).
USP 30—NF25, Disintegration, pp. 276-277, 2007.
USP 33—U.S. Pharmacopeia, General Chapter 701—Disintegration, 2008.
Orally Disintegrating Tablets, draft Food and Drug Administration Guidance, Apr. 2007.
Heng, Paul Wan Sia, Chem Pharm Bull, 47 (5) 633-638 (1999).
Koral, Tony, Radio Frequency Heating and Post-Baking, Biscuit World, Issue 4, vol. 7, Nov 2004.
Dielectric Heating with Microwave Energy, Püschner MikrowellenEnergietechnik, pp. 1-4, Jun. 2007.
Amin, Avani F., Emerging Treands in the Development of Orally Disintegrating Tablet Technology, Pharmainfo.net, vol. 4, Issue 1, Jan. 26, 2006; pp. 1-30.
Matthes, R.; "Chapter 49" from website: http://www.ilo.org/safework_bookshelf/english?content&nd=857170571; made available online Oct. 12, 2004.
Google page showing the availability date of web reference U; provided Mar. 15, 2011.
Rambali, B., et al., International Journal of Pharmaceutics 220 (2001), pp. 129-140.
Radio Frequency Company, Microwave, (Feb. 19, 2004), pp. 1-2.
Int'l Search Report for Application No. PCT/US2008/081496, dated Jul. 15, 2009.
Int'l Search Report for Application No. PCT/US2008/74375, dated Nov. 17, 2008.
Int'l Search Report for Application No. PCT/US2010/049909 dated Dec. 3, 2010.
Int'l Search Report for Application No. PCT/US2010/049915 dated Mar. 25, 2011.
Int'l Search Report for Application No. PCT/US2010/049925 dated Dec. 8, 2010.
Int'l Search Report for Application No. PCT/US2010/049931 dated Jan. 7, 2011.
Int'l Search Report for Application No. PCT/US2010/049933 dated Feb. 15, 2011.
Int'l Search Report for Application No. PCT/US2010/049964 dated Dec. 30, 2010.
Int'l Search Report for Application No. PCT/US2010/049971 dated Jan. 7, 2011.
Int'l Search Report for Application No. PCT/US2011/029155 dated Jun. 28, 2011.
Int'l Search Report for Application No. PCT/US2011/029158 dated Jun. 28, 2011.
Int'l Search Report for Application No. PCT/US2011/029161 dated Jun. 28, 2011.
Int'l Search Report for Application No. PCT/US2010/049974 dated Mar. 5, 2013.
U.S. Appl. No. 13/803,527, filed Mar. 14, 2013.
U.S. Appl. No. 13/804,109, filed Mar. 14, 2013.
U.S. Appl. No. 13/804,229, filed Mar. 14, 2013.
U.S. Appl. No. 13/804,410, filed Mar. 14, 2013.
International Search Report mailed Aug. 20, 2013 for corresponding Patent Application No. PCT/US2013/039045.
International Search Report mailed Aug. 21, 2013 for corresponding Patent Application No. PCT/US2013/039061.
International Search Report mailed Jun. 8, 2013 for corresponding Patent Application No. PCT/US2013/039047.
International Search Report mailed Nov. 7, 2013 for corresponding Application No. PCT/US2013/039040.
Heng, P., et al., Melt Processes for Oral Solid Dosage Forms', Encyclopedia of Pharmaceutical Technology, vol. 4, Jan. 2, 2007, pp. 2257-2261.
International Search Report mailed Aug. 20, 2031 for Application No. PCT/US2013/039045.
International Search Report mailed Aug. 21, 2013 for Application No. PCT/US2013/039061.
European Search Report mailed Aug. 1, 2013 for Application No. E{08798740.
Maltodextrin (Maltrin M580), Apr. 20, 2000, (PFormulate Excipients).

FIG. 1A  FIG. 1B  FIG. 1C
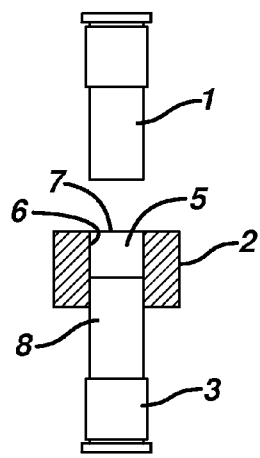 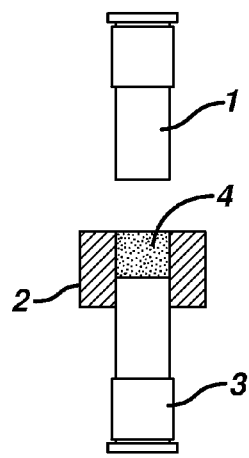 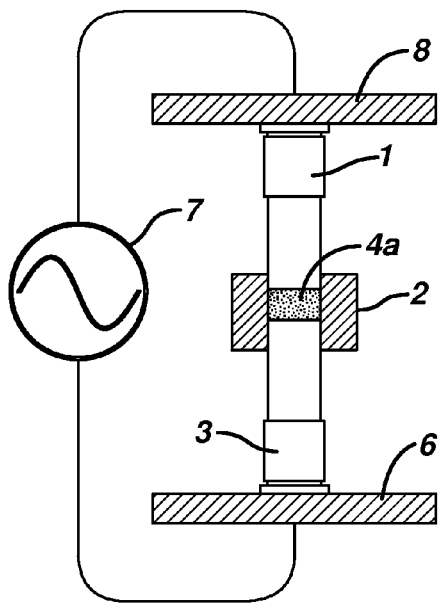
FIG. 1D  FIG. 1E  FIG. 1F
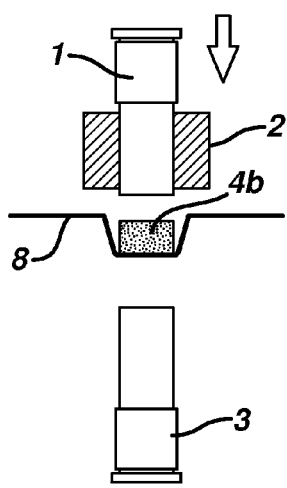 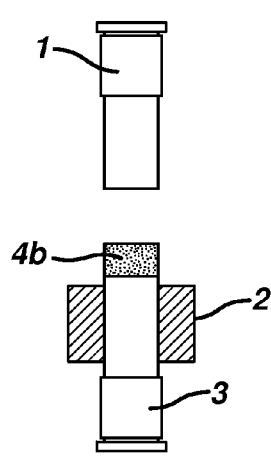 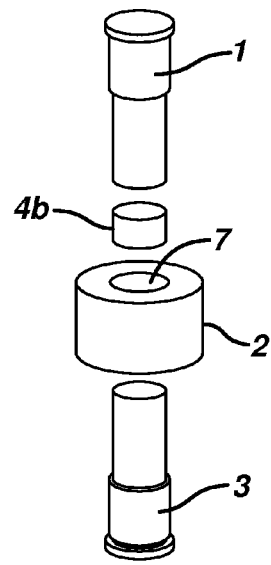

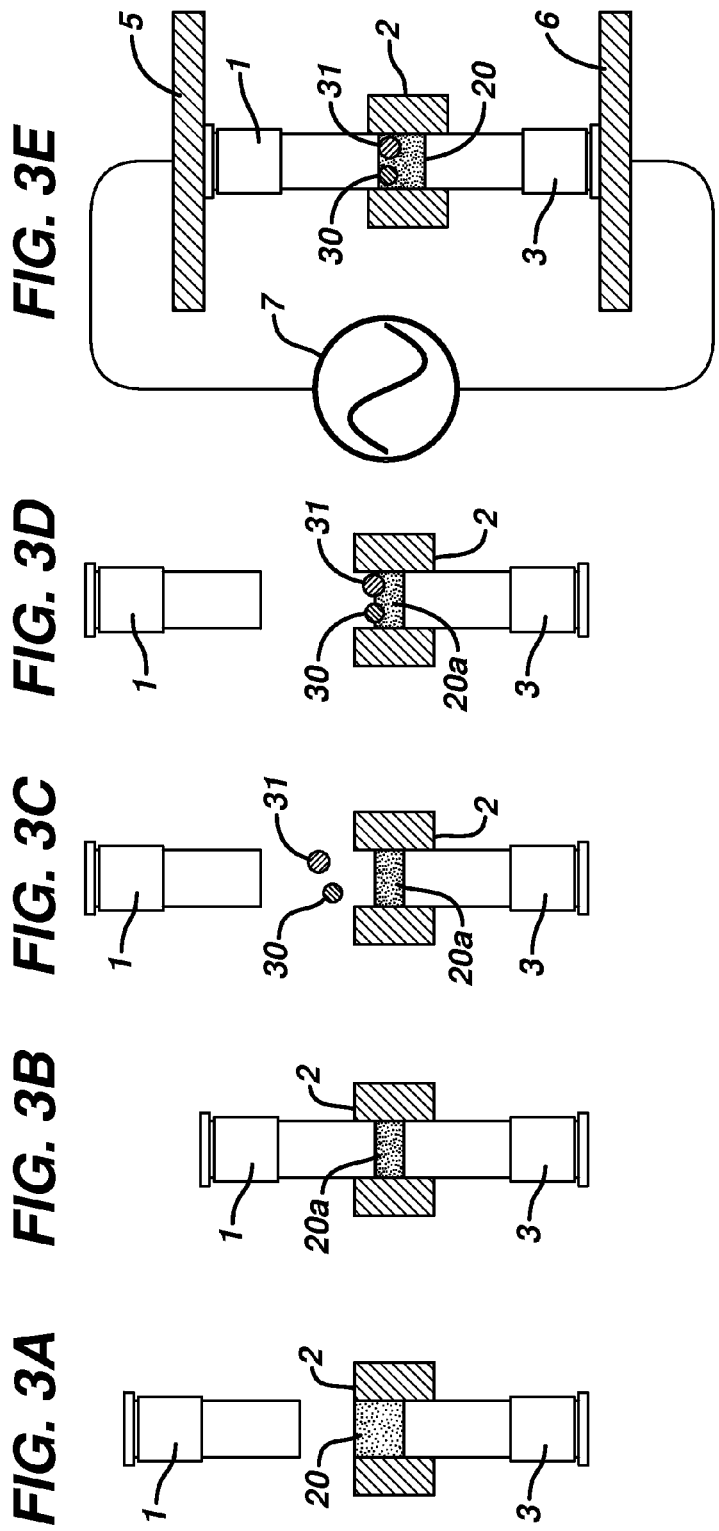

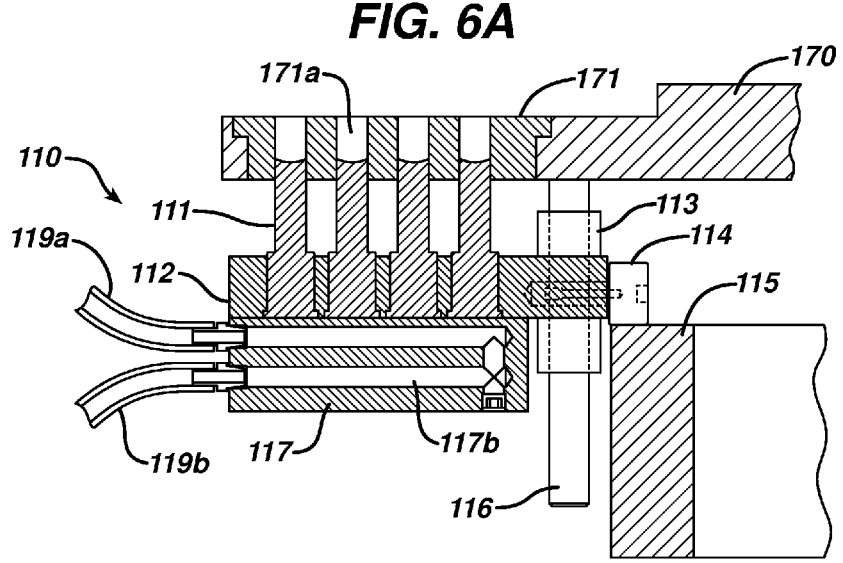
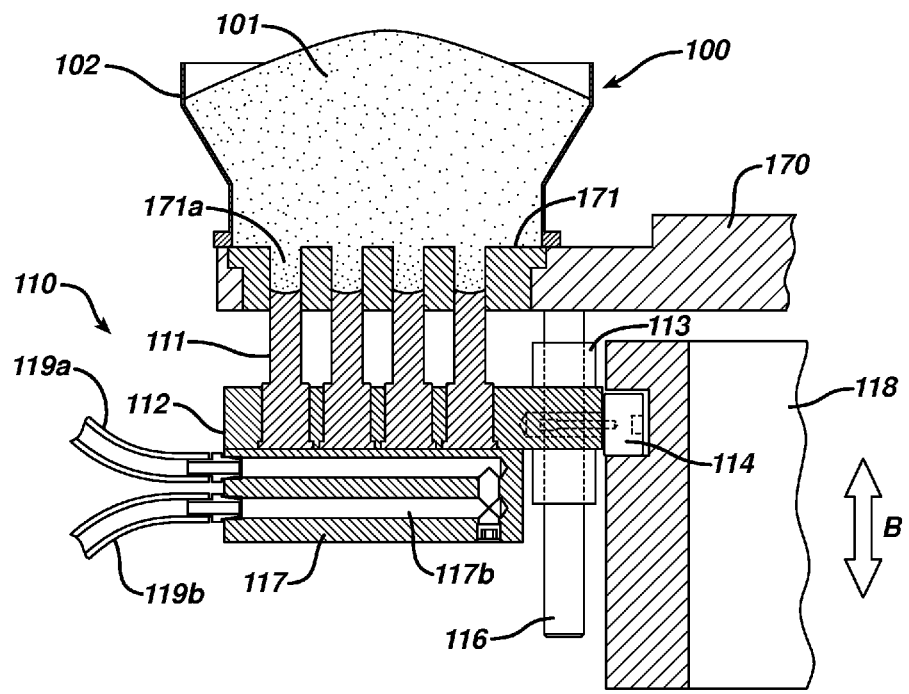

MANUFACTURE OF LOZENGE PRODUCT WITH RADIOFREQUENCY

CROSS REFERENCE TO RELATED APPLICATIONS

This application is a continuation of U.S. application Ser. No. 12/887,575, filed Sep. 22, 2010, now U.S. Pat. No. 8,343,533, which application claims priority of the benefits of the filing of U.S. Provisional Application Ser. No. 61/245,315, filed Sep. 24, 2009, U.S. Provisional Application Ser. No. 61/255,582, filed Oct. 28, 2009, U.S. Provisional Application Ser. No. 61/314,629, filed Mar. 17, 2010, and U.S. Provisional Application Ser. No. 61/358,167, filed Jun. 24, 2010. The complete disclosures of the aforementioned related U.S. patent applications are hereby incorporated herein by reference for all purposes.

BACKGROUND OF THE INVENTION

Lozenges are typically produced using a boiled mixture of sugar and/or corn syrup, wherein the mixture is heated and melted. However, certain materials are not compatible with such methods that use high heat for a significant amount of time, such as heat sensitive active ingredients and volatile flavor and sensate components. Such lozenges also have the disadvantage of using very moisture sensitive materials or retain a large amount of latent or bound water upon cooling into the final lozenge form. This may require expensive packaging which has low moisture permeability or the use of external desiccants. In addition, latent moisture can be an issue for certain active ingredients, particularly pharmaceutical active ingredient, where the formation of degradant compound can be accelerated upon stability.

Thus, there is a need for making lozenges which does not utilize the high temperatures and/or high amount of water content used in the typical boiling process.

SUMMARY OF THE INVENTION

In one aspect, the present invention features a process for making a lozenge product including the steps of forming a powder blend containing an amorphous carbohydrate polymer into the desired shape of the lozenge product and applying radiofrequency ("RF") energy to the shape for a sufficient period of time to soften or melt said amorphous carbohydrate polymer to fuse the shape into said lozenge product.

In other aspects, the present invention features lozenge products manufactured by such process and the use of lozenge products.

Other features and advantages of the present invention will be apparent from the detailed description of the invention and from the claims.

BRIEF DESCRIPTION OF THE FIGURES

FIGS. 1A-F are cross-section, side views of an embodiment of the invention showing the manufacture of lozenge shape 4a from powder blend 4 within die platen 2.

FIGS. 3A-G are cross-section, side views of an embodiment of the invention showing the manufacture of lozenge 40 containing preformed inserts 30 and 31 from powder blend 20 within die platen 2.

FIGS. 6A and 6B are section views of the lower forming tool assembly 110 in the start position of the manufacturing cycle.

FIG. 8 is a section view through the RF station rotary indexing machine 195 prior showing the manufacture of lozenges 101a.

DETAILED DESCRIPTION OF THE INVENTION

Figure 2A:
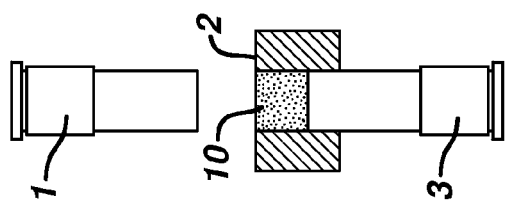
FIGS. 2A-H are cross-section, side views of an embodiment of the invention showing the manufacture of a bilayer lozenge 12 from powder blends 10 and 11 within die platen 2.

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

As discussed above, in one aspect, the present invention features a process for making a lozenge product including the steps of forming a powder blend containing an amorphous carbohydrate polymer into the desired shape of the lozenge product and applying RF energy to the shape for a sufficient period of time to soften or melt said amorphous carbohydrate polymer to fuse the shape into said lozenge product.

Powder Blend

As discussed above, the lozenge shape is manufactured by forming a powder blend containing an amorphous carbohydrate polymer and optionally nicotine and/or other pharmaceutically active agent(s) and/or excipients. Examples of such excipients include, but are not limited to, glidants, lubricants, sweeteners, flavors and aromatics, enhancers, coloring agents, preservatives, vitamins, minerals, fluoride, and tooth whitening agents, and mixtures thereof. One or more of the above ingredients may be present on the same particle of the powder blend.

Suitable lubricants include, but are not limited to, long chain fatty acids and their salts, such as magnesium stearate and stearic acid, talc, glycerides waxes, and mixtures thereof.

Suitable glidants include, but are not limited to, colloidal silicon dioxide.

Examples of sweeteners include, but are not limited to, synthetic or natural sugars; artificial sweeteners such as saccharin, sodium saccharin, aspartame, acesulfame, thaumatin, glycyrrhizin, sucralose, dihydrochalcone, alitame, miraculin, monellin, and stevside; sugar alcohols such as sorbitol, mannitol, glycerol, lactitol, maltitol, and xylitol; sugars extracted from sugar cane and sugar beet (sucrose), dextrose (also called glucose), fructose (also called laevulose), and lactose (also called milk sugar); isomalt, salts thereof, and mixtures thereof.

Examples of flavors and aromatics include, but are not limited to, essential oils including distillations, solvent extractions, or cold expressions of chopped flowers, leaves, peel or pulped whole fruit comprising mixtures of alcohols, esters, aldehydes and lactones; essences including either diluted solutions of essential oils, or mixtures of synthetic chemicals blended to match the natural flavor of the fruit (e.g., strawberry, raspberry and black currant); artificial and natural flavors of brews and liquors, e.g., cognac, whisky, rum, gin, sherry, port, and wine; tobacco, coffee, tea, cocoa, and mint; fruit juices including expelled juice from washed, scrubbed fruits such as lemon, orange, and lime; spear mint, pepper mint, wintergreen, cinnamon, cacoe/cocoa, vanilla, liquorice, menthol, eucalyptus, aniseeds nuts (e.g., peanuts, coconuts, hazelnuts, chestnuts, walnuts, colanuts), almonds, raisins; and powder, flour, or vegetable material parts including tobacco plant parts, e.g., genus *Nicotiana*, in amounts not contributing significantly to the level of nicotine, and ginger.

Examples of coloring agents include, but are not limited to, dyes being approved as a food additive.

Amorphous Carbohydrate Polymer

The powder blend/lozenge shape/lozenge product contains at least one amorphous carbohydrate polymer. What is meant by an "amorphous carbohydrate polymer" is a molecule having a plurality of carbohydrate monomers wherein such molecule has a crystallinity of less than 20%, such as less than 10%, such as less than 5%. Examples of amorphous carbohydrate polymers include, but are not limited to hydrogenated starch hydrolysate, polydextrose, and oligosaccharides. Examples of oligosaccharides include, but are not limited to, fructo-oligosaccharide, galacto-oligosaccharide malto-oligosaccharide, inulin, and isolmalto-oligosaccharide.

In one embodiment, the amount of amorphous carbohydrate polymer in the powder blend/lozenge shape/lozenge product is from about 50 percent to about 99.9 percent, by weight, such as from about 80 percent to about 95 percent by weight.

In one embodiment the powder blend/lozenge shape/lozenge product contains less than about 20 percent by weight of crystalline material, such as less than 10 percent, such as less than 5 percent, such as none. In one embodiment the lozenge is substantially free of isomalt.

Nicotine Compound

In one embodiment, the powder blend/lozenge shape/lozenge product contains a smoking cessation compound(s) such as: nicotine and/or metabolites thereof, such as cotinine, nicotine N'-oxide, nornicotine, (S)-nicotine-N-β-glucuronide or salt thereof (hereinafter "nicotine compound"); varenicline, bupropion, nortriptyline, doxepin, fluoxetine, imipramine, moclobemide, conotoxinMII, epibatidine, A-85380, lobeline, anabasine, SIB-1508Y, SIB-1553A, ABT-418, ABT-594, ABT-894, TC-2403, TC-2559, RJR-2403, SSR180711, GTS-21, and/or cytisine or salts thereof. The smoking cessation compound (e.g., nicotine compound) may be present in the powder blend and/or the optional coating.

Numerous nicotine salts are known and may be used. Examples include, but are not limited to, formic (2:1), acetic (3:1), propionic (3:1), butyric (3:1), 2-methylbutyric (3:1), 3-methylbutyric (3:1), valeric (3:1), lauric (3:1), palmitic (3:1), tartaric (1:1) and (2:1), citric (2:1), malic (2:1), oxalic (2:1), benzoic (1:1), gentisic (1:1), gallic (1:1), phenylacetic (3:1), salicylic (1:1), phthalic (1:1), picric (2:1), sulfosalicylic (1:1), tannic (1:5), pectic (1:3), alginic (1:2), hydrochloric (2:1), chloroplatinic (1:1), silcotungstic (1:1), pyruvic (2:1), glutamic (1:1), and aspartic (1:1) salts of nicotine.

In one embodiment, the nicotine compound is bound to a resin (e.g., a polyacrylate resin), zeolite, or cellulose or starch microsphere. Examples of cation exchange resins include, but are not limited to, Amberlite IRC 50 (Rohm & Haas), Amberlite IRP 64 (Rohm & Haas), Amberlite IRP 64M (Rohm & Haas), BIO-REX 70 (BIO-RAD Lab.), Amberlite IR 118 (Rohm & Haas), Amberlite IRP 69 (Rohm & Haas), Amberlite IRP 69M (Rohm & Haas), BIO-REX 40 (BIO-RAD Lab.), Amberlite IR 120 (Rohm & Haas), Dowex 50 (Dow Chemical), Dowex 50W (Dow Chemical), Duolite C 25 (Chemical Process Co.), Lewatit S 100 (Farbenfabriken Bayer), Ionac C 240 (Ionac Chem.), Wofatit KP S 200 (I.G. Farben Wolfen), Amberlyst 15 (Rohm & Haas), Duolite C-3 (Chemical Process), Duolite C-10 (Chemical Process), Lewatit KS (Farbenfabriken Bayer), Zerolit 215 (The Permutit Co.), Duolite ES-62 (Chemical Process), BIO-REX 63 (BIO-RAD Lab.), Duolite ES-63 (Chemical Process), Duolite ES-65 (Chemical Process), Ohelex 100 (BIO-RAD Lab.), Dow Chelating Resin A-1 (Dow Chemical Company), Purolite C115HMR (Purolite International Ltd.), CM Sephadex C-25 (Pharmacia Fine Chemicals), SE Sephadex C-25 (Pharmacia Fine Chemicals), Viscarin GP-109NF Lambda-carrageenan FMC Biopolymer or any other anionic polyelectrolyte.

In one another embodiment, the nicotine compound is in the form of an inclusion complex with a cyclodextrin, which may include cyclodextrin complexation, such as complexation of the active pharmaceutically compound with cyclodextrin where preferably the cyclodextrin used is chosen among α-, β- and γ-cyclodextrin, the hydroxypropyl derivatives of α-, β- and γ-cyclodextrin, sulfoalkylether cyclodextrins such as sulfobutylether β-cyclodextrin, alkylated cyclodextrins such as the randomly methylated β-cyclodextrin, and various branched cyclodextrins such as glucosyl- and maltosyl-β-cyclodextrin.

In one embodiment, the nicotine compound is dosed in the lozenge product to provide the person with a dose to achieve an effect, e.g., to provide a sense of smoking satisfaction without smoking and/or to reduce of the urge to smoke or use tobacco. This amount may, of course, vary from person to person.

In one embodiment, lozenge product includes the nicotine compound in an amount of from about 0.05 to about 12 mg calculated as the free base form of nicotine per lozenge product, such as from about 0.2-6 mg, such as from about 0.5-5 mg. This may in different embodiments include 0.05, 0.5, 1, 1.5, 2, 3, 4, 4.5, 5, 6, 7, 8, 9, 10, or 12 mg calculated as the free base form of nicotine per lozenge product.

Buffering Agent

In one embodiment, the lozenge/powder blend/coating contains both nicotine and a buffering agent. In one embodiment, the lozenge is buffered such that upon administration of the lozenge, the pH of the saliva is transiently increased from about 0.2 to about 4 pH units, preferably from about 0.4 to about 2 pH units. The buffering is designed so as to achieve a transient buffering of the saliva of a subject during use of the lozenge product. As the change is transient, the pH will return to its normal value after a certain period of time.

Examples of buffering agents include, but are not limited to, carbonates including carbonate, bicarbonate or sesquicarbonate, glycinate, phosphate, glycerophosphate or citrate of an alkali metal, such as potassium or sodium, or ammonium such as trisodium or tripotassium citrate, trisodium phosphate, disodium hydrogen phosphate, tripotassium phosphate, dipotassium hydrogen phosphate, calcium hydroxide, sodium glycinate, and trometamol (TRIS). Alkali metal carbonates, glycinates and phosphates are preferred buffering agents.

The one or more buffering agents may to some extent be microencapsulated or otherwise coated as granules with polymers and/or lipids being less soluble in saliva than is the one or more buffering agents. Such microencapsulation controls the dissolution rate whereby is extended the time frame of the buffering effect.

In order to increase the buffering capacity still further without correspondingly increasing the pH, one may in specific embodiments use a second or auxiliary buffering agent to the first buffering agent, such as e.g., sodium or potassium bicarbonate buffers. The second or auxiliary buffering agent may be selected from the group consisting of alkali metal bicarbonates that are preferred for this purpose. Thus, further embodiments of the invention may include a mixture of an alkali metal carbonate or phosphate and alkali metal bicarbonate.

The amount of the buffering agent or agents in the lozenge composition is preferably sufficient in the specific embodiments to raise the pH of the saliva to above 7, as specified above, to transiently maintain the pH of the saliva in the oral cavity above 7, e.g., pH 7-10.

The nicotine may be administered in different forms, e.g., in different complexes or salts. The amount of buffer required to achieve such an increase in pH of the different administered nicotine form is readily calculated by the skilled man in the art. The extent and duration of the increase in pH is dependent on type and amount of the buffering agent(s) used as well as where the buffer is distributed in the chewing gum product.

Pharmaceutically Active Agent

The powder blend/lozenge shape/lozenge product of the present invention may includes at least one pharmaceutically active agent (other than or in addition to a nicotine compound). What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antipyretics, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, and sedatives.

Examples of suitable gastrointestinal treating agents include, but are not limited to: antacids such as aluminum-containing pharmaceutically active agents (e.g., aluminum carbonate, aluminum hydroxide, dihydroxyaluminum sodium carbonate, and aluminum phosphate), bicarbonate-containing pharmaceutically active agents, bismuth-containing pharmaceutically active agents (e.g., bismuth aluminate, bismuth carbonate, bismuth subcarbonate, bismuth subgallate, and bismuth subnitrate), calcium-containing pharmaceutically active agents (e.g., calcium carbonate), glycine, magnesium-containing pharmaceutically active agents (e.g., magaldrate, magnesium aluminosilicates, magnesium carbonate, magnesium glycinate, magnesium hydroxide, magnesium oxide, and magnesium trisilicate), phosphate-containing pharmaceutically active agents (e.g., aluminum phosphate and calcium phosphate), potassium-containing pharmaceutically active agents (e.g., potassium bicarbonate), sodium-containing pharmaceutically active agents (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole, dextansoprazole, esomeprazole, pantoprazole, rabeprazole, and lansoprazole; gastrointestinal cytoprotectives, such as sucraflate and misoprostol; gastrointestinal prokinetics such as prucalopride; antibiotics for *H. pylori*, such as clarithromycin, amoxicillin, tetracycline, and metronidazole; antidiarrheals, such as bismuth subsalicylate, kaolin, diphenoxylate, and loperamide; glycopyrrolate; analgesics, such as mesalamine; antiemetics such as ondansetron, cyclizine, diphenyhydroamine, dimenhydrinate, meclizine, promethazine, and hydroxyzine; probiotic bacteria including but not limited to lactobacilli; lactase; racecadotril; and antiflatulents such as polydimethylsiloxanes (e.g., dimethicone and simethicone, including those disclosed in U.S. Pat. Nos. 4,906,478, 5,275,822, and 6,103,260); isomers thereof; and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Examples of antihistamines and decongestants, include, but are not limited to, bromopheniramine, chlorocyclizine, dexbrompheniramine, bromohexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxalamide, xylometazoline, loratadine, desloratadine, and cetirizine; isomers thereof; and pharmaceutically acceptable salts and esters thereof.

Examples of cough suppressants and expectorants include, but are not limited to, diphenhydramine, dextromethorphan, noscapine, chlophedianol, menthol, benzonatate, ethylmorphine, codeine, acetylcysteine, carbocisteine, ambroxol, belladonna alkaloids, sobrenol, guaiacol, and guaifenesin; isomers thereof; and pharmaceutically acceptable salts and prodrugs thereof.

Examples of muscle relaxants include, but are not limited to, cyclobenzaprine and chlorzoxazone metaxalone, orphenadrine, and methocarbamol; isomers thereof; and pharmaceutically acceptable salts and prodrugs thereof.

Examples of stimulants include, but are not limited to, caffeine.

Examples of sedatives include, but are not limited to sleep aids such as antihistamines (e.g., diphenhydramine), eszopiclone, and zolpidem, and pharmaceutically acceptable salts and prodrugs thereof.

Examples of appetite suppressants include, but are not limited to, phenylpropanolamine, phentermine, and diethylcathinone, and pharmaceutically acceptable salts and prodrugs thereof.

Examples of anesthetics (e.g., for the treatment of sore throat) include, but are not limited to dyclonine, benzocaine, and pectin and pharmaceutically acceptable salts and prodrugs thereof.

Examples of suitable statins include but are not limited to atorvastin, rosuvastatin, fluvastatin, lovastatin, simvastatin, atorvastatin, pravastatin and pharmaceutically acceptable salts and prodrugs thereof.

In one embodiment, the powder blend includes phenylephrine, dextromethorphan, pseudoephedrine, chlorpheniramine, methocarbomal, chlophedianol, ascorbic acid, menthol, pectin, dyclonine, or benzocaine, or pharmaceutically acceptable salts thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (e.g., hydrates) or common organic solvents, and such solvates are also intended to be encompassed within the scope of this invention.

In one embodiment, the pharmaceutically active agent or agents are present in the lozenge product in a therapeutically effective amount, which is an amount that produces the desired therapeutic response upon oral administration and can be readily determined by one skilled in the art. In determining such amounts, the particular pharmaceutically active agent being administered, the bioavailability characteristics of the pharmaceutically active agent, the dose regime, the age and weight of the patient, and other factors must be considered, as known in the art.

The pharmaceutically active agent may be present in various forms. For example, the pharmaceutically active agent may be dispersed at the molecular level, e.g. melted, within the lozenge product, or may be in the form of particles, which in turn may be coated or uncoated. If the pharmaceutically active agent is in form of particles, the particles (whether coated or uncoated) typically have an average particle size of from about 1 to about 2000 microns. In one embodiment, such particles are crystals having an average particle size of from about 1 to about 300 microns. In another embodiment, the particles are granules or pellets having an average particle size of from about 50 to about 2000 microns, such as from about 50 to about 1000 microns, such as from about 100 to about 800 microns.

The pharmaceutically active agent may be present in pure crystal form or in a granulated form prior to the addition of the taste masking coating. Granulation techniques may be used to improve the flow characteristics or particle size of the pharmaceutically active agents to make it more suitable for compaction or subsequent coating. Suitable binders for making the granulation include but are not limited to starch, polyvinylpyrrolidone, polymethacrylates, hydroxypropylmethylcellulose, and hydroxypropylcellulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation.

If the pharmaceutically active agent has an objectionable taste, the pharmaceutically active agent may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked pharmaceutically active agents may also be employed. For example, acetaminophen particles, which are encapsulated with ethylcellulose or other polymers by a coacervation process, may be used in the present invention. Coacervation-encapsulated acetaminophen may be purchased commercially from Eurand America, Inc. (Vandalia, Ohio) or from Circa Inc. (Dayton, Ohio).

In one embodiment one or more pharmaceutically active agents or a portion of the pharmaceutically active agent may be bound to an ion exchange resin for the purposes of taste-masking the pharmaceutically active agent or delivering the active in a modified release manner.

The susceptibility to energy of the pharmaceutically active agent (e.g., to melt or degrade) can have an impact on the type of energy and/or temperature used during the heating step as well as the type of the amorphous carbohydrate polymer used.

In one embodiment, the processing of the lozenge product is free of a wet or hot melt granulation step. In this embodiment, the materials are directly blended prior to the addition of heat. In one embodiment, the materials are directly blended and compressed prior to the addition of heat.

Manufacture of Lozenge Shape

In one embodiment, the powder blend is fed into the die of an apparatus that applies pressure to form the lozenge shape (e.g., by light compaction such as tamping). Any suitable compacting apparatus may be used, including, but not limited to, a conventional unitary or rotary tablet press. In one embodiment, the lozenge shape may be formed by compaction using a rotary tablet press (e.g., such as those commercially available from Fette America Inc., Rockaway, N.J. or Manesty Machines LTD, Liverpool, UK). In one embodiment, the lozenge shape is heated after it is removed from the tablet press. In another embodiment, the lozenge shape is heated within the tablet press.

In most thermodynamic processes or machines, the heat source and the heat sink are two distinct machines or steps requiring material to be transferred from one apparatus to the other. In the manufacture of the lozenges of the present invention, the energy must be added to the lozenge to achieve the binding effect and then must be removed from the product to solidify and strengthen it for its final handling packaging and use. One of the unique and unanticipated attributes of one embodiment of the manufacturing process of the present invention is that heat source and heat sink are part of the same apparatus. In one embodiment, heat is added to the forming tools to achieve proper sintering at the surface as well as at the center of the lozenge.

To exploit this unique thermal effect, powder blends can also be chosen for their thermal properties and thermal conductivity and specific heat such that the powder blend particles themselves become heat sinks. The desirable result of this is that the total process time can be just a few seconds and that the lozenge does not need to be transferred from the die platen during the critical tamping and heating process. The die platen can function then as a material handling apparatus as well as a thermal forming tool.

In one embodiment, the compaction step (e.g., tamping) which occurs prior to the addition of the RF energy utilizes a compaction force which is less than the force required to compress a chewable or swallowable tablet. In one embodiment, the compaction force is less than about 1000 pounds per square inch (e.g., less than about 500 pounds per square inch, such as less than 200 pounds per square inch, such as less than 50 pounds per square inch). In one embodiment, the energy is applied while the powder blend is under such force.

In one embodiment, the compaction step occurs in an indexed manner, where one set of lozenges are compacted simultaneously, before rotating to another indexing station. In one embodiment, the compaction step occurs at a single indexing station and the application of RF energy occurs at a separate indexing station. In another embodiment, a third indexing station is present wherein the ejection of the lozenge or multiple lozenges occurs, wherein the lower forming tool is raised up through and up to the surface of the die. In another embodiment the compaction step is performed through the addition of air pressure or hydraulic cylinder to the top of the upper forming tools. In one embodiment multiple lozenges are ejected simultaneously and separated from the surface of the indexing station and removed via a take-off bar.

In another embodiment, the lozenge shape may be prepared by the compaction methods and apparatus described in United States Patent Application Publication No. 20040156902. Specifically, the lozenge shape may be made using a rotary compression module including a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional powder blend recovery system to recover excess powder blend from the filters and return the powder blend to the dies. In one embodiment the RF energy source is projected through the die table of a rotary press into the appropriate electrode within the forming tool or the forming cavity. In one embodiment the die table is constructed of non-conductive material.

In one embodiment, the lozenge shape is prepared by the compaction methods and apparatus described in issued U.S. Pat. No. 6,767,200. Specifically, the lozenge shape is made using a rotary compression module including a fill zone, compression zone, and ejection zone in a single apparatus having a double row die construction as shown in FIG. 6 therein. The dies of the compression module are preferably filled using the assistance of a vacuum, with filters located in or near each die.

The lozenge shape may have one of a variety of different shapes. For example, the lozenge shape may be shaped as a polyhedron, such as a cube, pyramid, prism, or the like; or may have the geometry of a space figure with some non-flat faces, such as a cone, truncated cone, triangle, cylinder, sphere, torus, or the like. In certain embodiments, a lozenge shape has one or more major faces. For example, the lozenge shape surface typically has opposing upper and lower faces formed by contact with the upper and lower forming tool faces (e.g., die punches) in the compaction machine. In such embodiments, the lozenge shape surface typically further includes a "belly-band" located between the upper and lower faces, and formed by contact with the die walls in the compaction machine. A lozenge shape/lozenge may also be a multilayer. Applicants have found that sharp edges in the tooling used to make the lozenges can cause arcing, and thus more rounded edges may be needed.

In one embodiment, the method of producing the lozenge shape is substantially free of the use of solvents. In this embodiment, the powder blend is substantially free of solvents, and the manufacturing process (e.g., filling process into the die) is also substantially free of solvents. Solvents may include, but are not limited to, water, organic solvents such as but not limited to alcohols, chlorinated solvents, hexanes, or acetone; or gaseous solvents such as but not limited to nitrogen, carbon dioxide or supercritical fluids.

In one embodiment a vibratory step is utilized (e.g., added after filling of the powder blend but prior to the heating or fusing step, in order to remove air from the powder blend). In one embodiment a vibration with the frequency from about 1 Hz to about 50 KHz is added with amplitude from 1 micron to 5 mm peak-to-peak to allow for the flowable powder blend to settle into the cavity of a the die platen ("forming cavity").

In one embodiment, as shown in FIGS. 1A-1F, a metered volume of powder blend 4 is filled into a Teflon® (or similar electrical and RF energy insulative material such as ceramic or UHMW plastic) die platen 2. Die platen 2 has forming cavity 5 with inner wall 6, upper opening 7 on the upper surface of die platen 2 (which allows powder blend 4 and upper forming tool 1 to move into the forming cavity 5), and lower opening 8 on the opposite surface of die platen 2 (which allows powder blend 4 and lower forming tool 3 to move into the forming cavity 5). Powder blend 4 may be either gravity fed or mechanically fed from a feeder (not shown). A metallic, electrically conductive lower forming tool 3 is inserted into the die platen to retain the powder blend 4, within die platen 2. A similar metallic, electrically conductive upper forming tool 1 is positioned above the die platen 2 as shown in FIG. 1B. The forming tools 1 and 3, die platen 2, and powder blend 4 are then moved to a compaction and RF heating station as shown in FIG. 1C to form lozenge shape 4a.

This heating station is comprised of an RF generator 7 which produces the necessary high voltage, high frequency energy. The generator 7 is electrically connected to movable upper RF electrode plate 8 and movable lower RF electrode plate 6. As shown in FIG. 1C, at this position, the powder blend 4 is compacted between an upper forming tool 1 and a lower forming tool 3 by pressure exerted by upper RF electrode plate 8 and lower electrode plate 6 to form lozenge shape 4a. Lozenge shape 4a is then exposed to RF energy from RF generator 7, which heats the amorphous carbohydrate polymer within lozenge shape 4a. After the RF energy is switched off, lozenge shape 4a cools to form the lozenge 4b. In one embodiment, as shown in FIG. 1D, lozenge 4b is pushed by upper forming tool 1 from the die platen 2 into blister 8, which is used to package lozenge 4b. In an alternative embodiment, as shown in FIG. 1E, lozenge 4b is pushed from the die platen 2 by the lower forming tool 3 and guided to an ejection chute by a stationary "take-off" bar (not shown). FIG. 1F shows a 3 dimensional representation of the forming tools 1 and 4, die platen 2, and lozenge 4b.

Figure 2B:
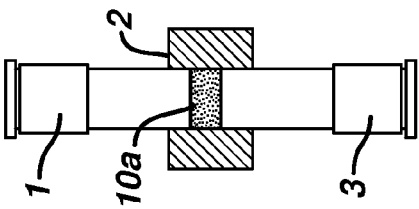
Figure 2C:
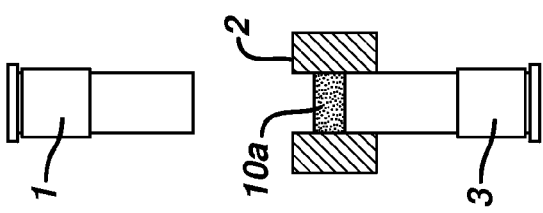
Figure 2D:
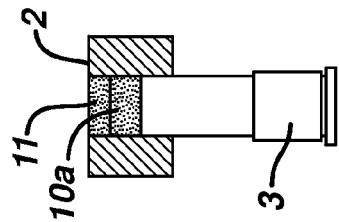
Figure 2E:
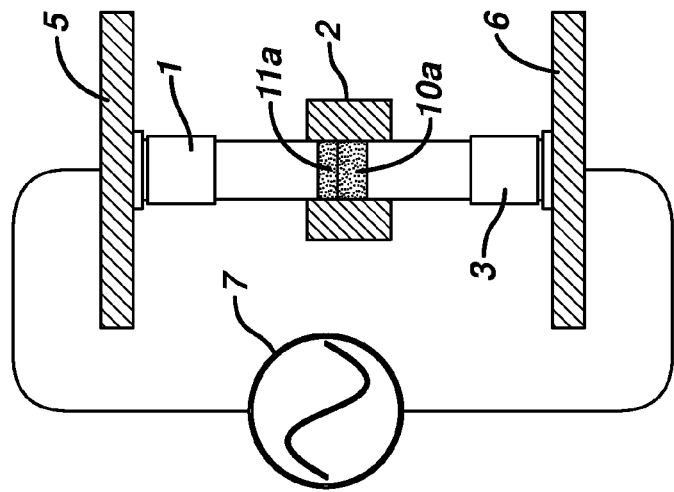
Figure 2F:
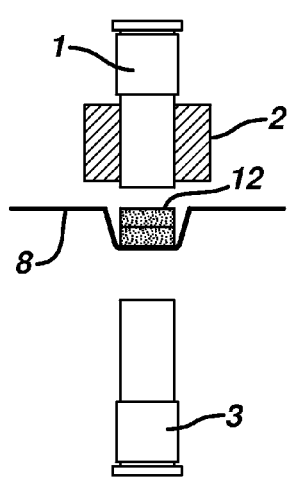
Figure 2G:
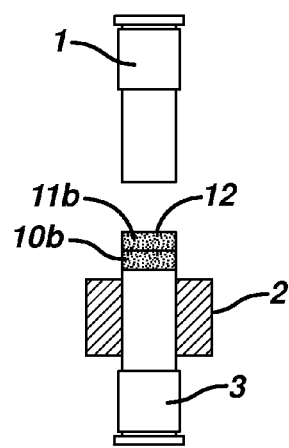
Figure 2H:
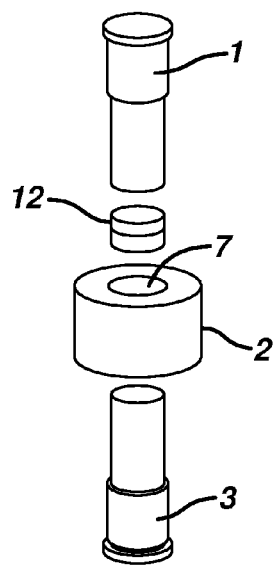

In FIGS. 2A-2H, an alternate embodiment of the invention is shown where a multilayer lozenge is produced. First, powder blend 10 is filled into die platen 2 as shown in FIG. 2A. Powder blend 10 is tamped or moved down into die platen 2 by upper forming tool 1 as shown in FIG. 2B to form lozenge shape 10a. Then, powder blend 11 is then filled on top of lozenge shape 10a. The forming tools 1 and 3, die platen 2, lozenge shape 10a and powder blend 11 are then moved to the compaction and RF heating station as shown in FIG. 2E. RF heating is accomplished as described above in FIG. 1C to produce multilayer lozenge 12 as shown in FIGS. 2F and 2G. While a bi-layer lozenge is shown in the drawing, additional multiple layers can be produced by adding additional powder blends to die platen 2.

Figure 3F:
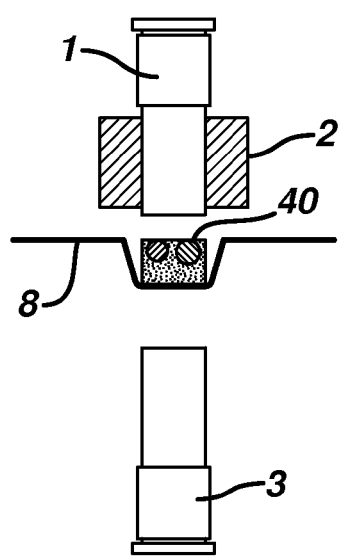
Figure 3G:
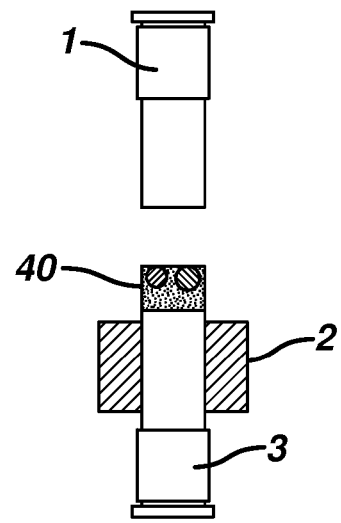

FIGS. 3A-3G show another embodiment of the invention where preformed inserts 30 and 31 are inserted into lozenge shape 20a as shown in FIGS. 3A-3D. Forming tools 1 and 3, die platen 2, lozenge shape 20, and preformed inserts 30 and 31 are then moved to the compaction and RF heating station as shown in FIG. 3E. RF heating is accomplished as described above in FIG. 1C to produce a multi-component lozenge 40 shown in FIGS. 2F and 2G.

Figure 4A:
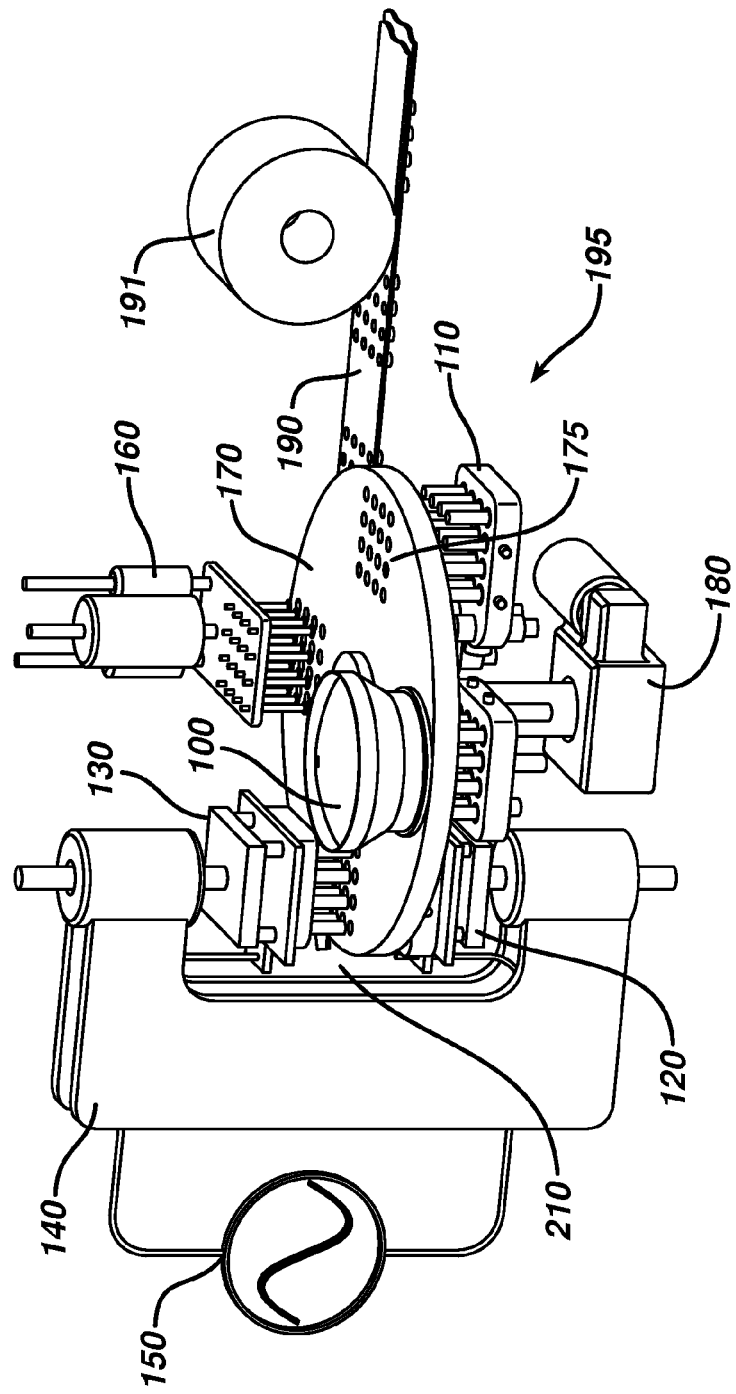
FIGS. 4A and 4B are a perspective view of a rotary indexing machine 195.
Figure 4B:
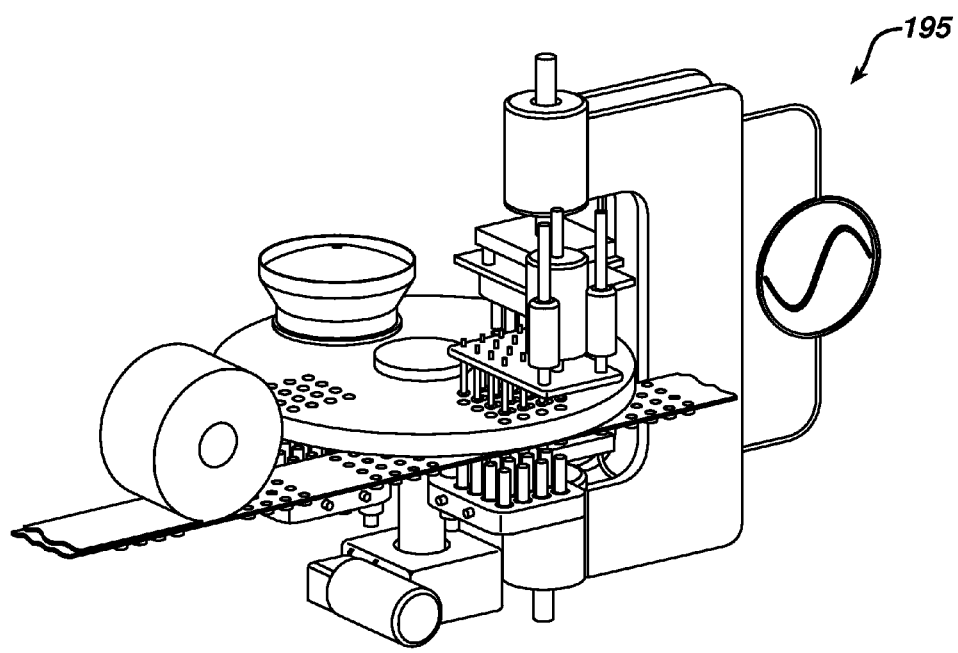

FIGS. 4A and 4B show two views of a rotary indexing machine 195 which is designed to create large quantities of lozenges. This embodiment of the invention is comprised of an indexing table 170 having four sets of die platens 175 each having sixteen cavities, powder feeder 100, RF generator 150, a machine frame 140, moving RF electrode assemblies 120 and 130, lower forming tool assembly 110, upper forming tool assembly 210, lozenge ejection station 160, indexer drive system 180, blister package web 190, and blister lid material roll 191.

Figure 5A:
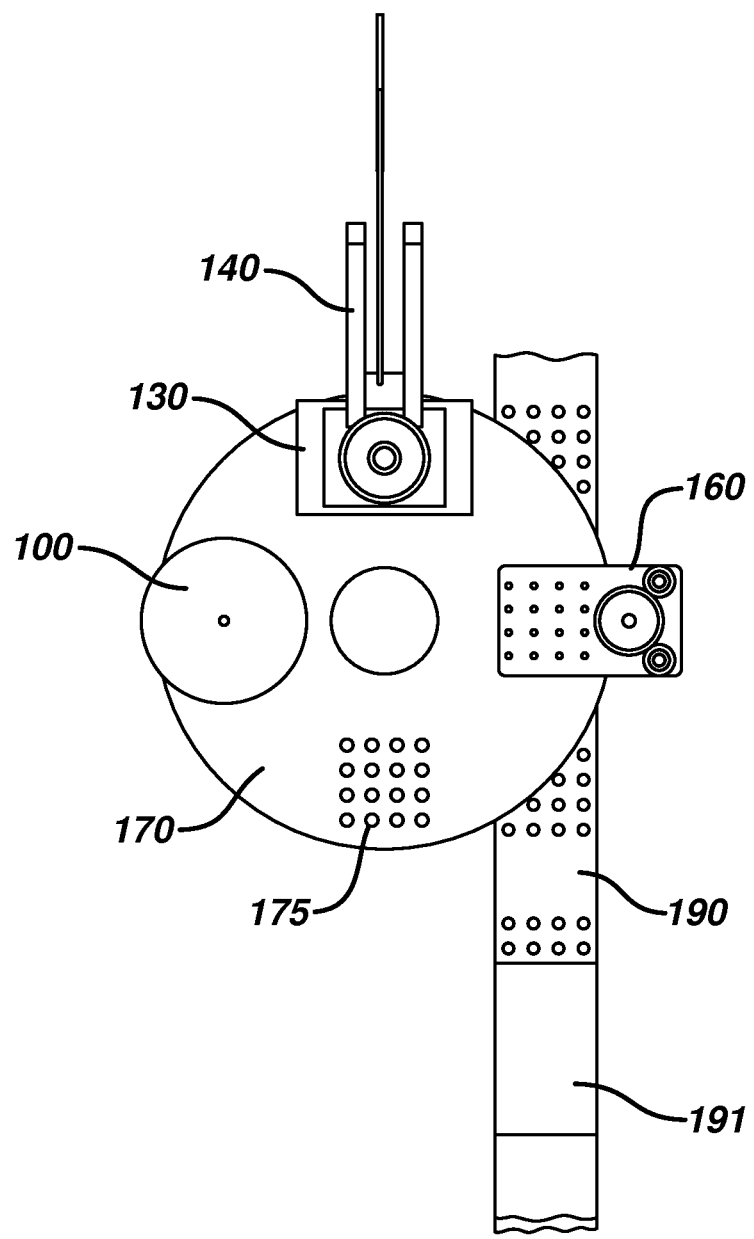
FIGS. 5A and 5B are top views of the rotary indexing machine 195 in the dwell position.
Figure 5B:
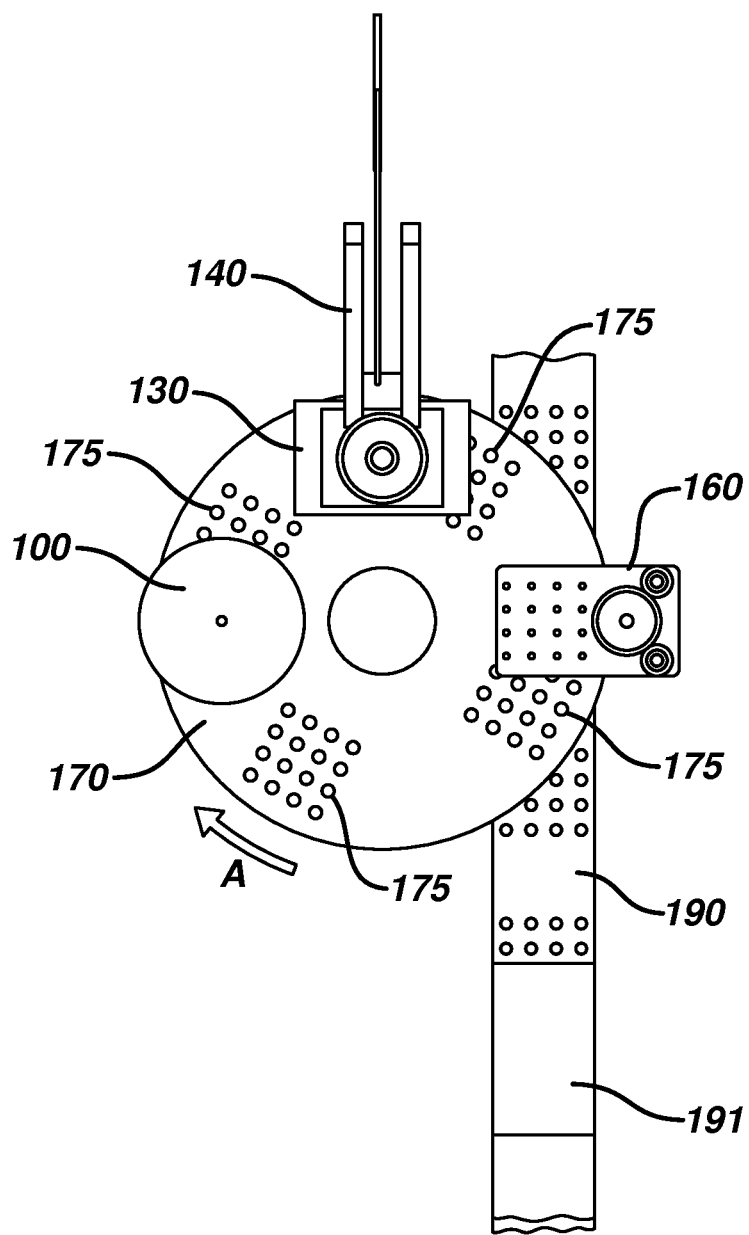

FIG. 5A is a top view of the apparatus in the dwell position. FIG. 5B is a top view of the apparatus as the indexing table 170 rotates between stations in direction "A". FIG. 6A depicts a section view through the lower forming tool assembly 110 in a start position of the manufacturing cycle. The lower forming tools 111, which are made of an electrically conductive metallic material such as brass or stainless steel, are retained in retainer plate 112 (e.g., made of aluminum or steel). Heated block 117 is attached to the retainer plate 112 and contains fluid passages 117b. Heated (or optionally cooling) fluid is circulated through the heated block 117 by connections to flexible hoses 119a and 119b which form a supply and return circuit. Heating can also be accomplished by electric cartridge heaters or other suitable means (not shown).

Attached to the retainer plate are cam-follower 114 and linear bearing 113. A guide shaft 116 is fixed to indexing table 170. The retainer plate and forming tools 111 and are moveable up or down according to the profile of barrel cam 115 which cam follower 114 rolls upon. Also shown is die platen 171, which is made of electrical and RF energy insulative material such as Teflon, UHMW, or ceramic. This is necessary to prevent a short circuit when the electrically conductive forming tools are positioned in the RF electric field in subsequent steps. The forming cavity 171a is shown empty at this stage of the process.

FIG. 6B depicts a section through the powder feeder station 100 of the apparatus. In this station powdered powder blend 101 is gravity fed into die platen 171. Movable cam segment 118 is adjusted up or down in direction "B" to vary the volume of the forming cavity 171a by changing the amount that the lower forming tools 111 penetrate into the die platen 171. This adjustable volume feature enables the precise dose of powdered powder blend to be selected for a desired lozenge weight. When the machine indexes out of the powder feeder station, the rim of feeder 102 scrapes against the die platen 171 to create a level powder surface relative to the surface of the die platen 171.

Figure 7:
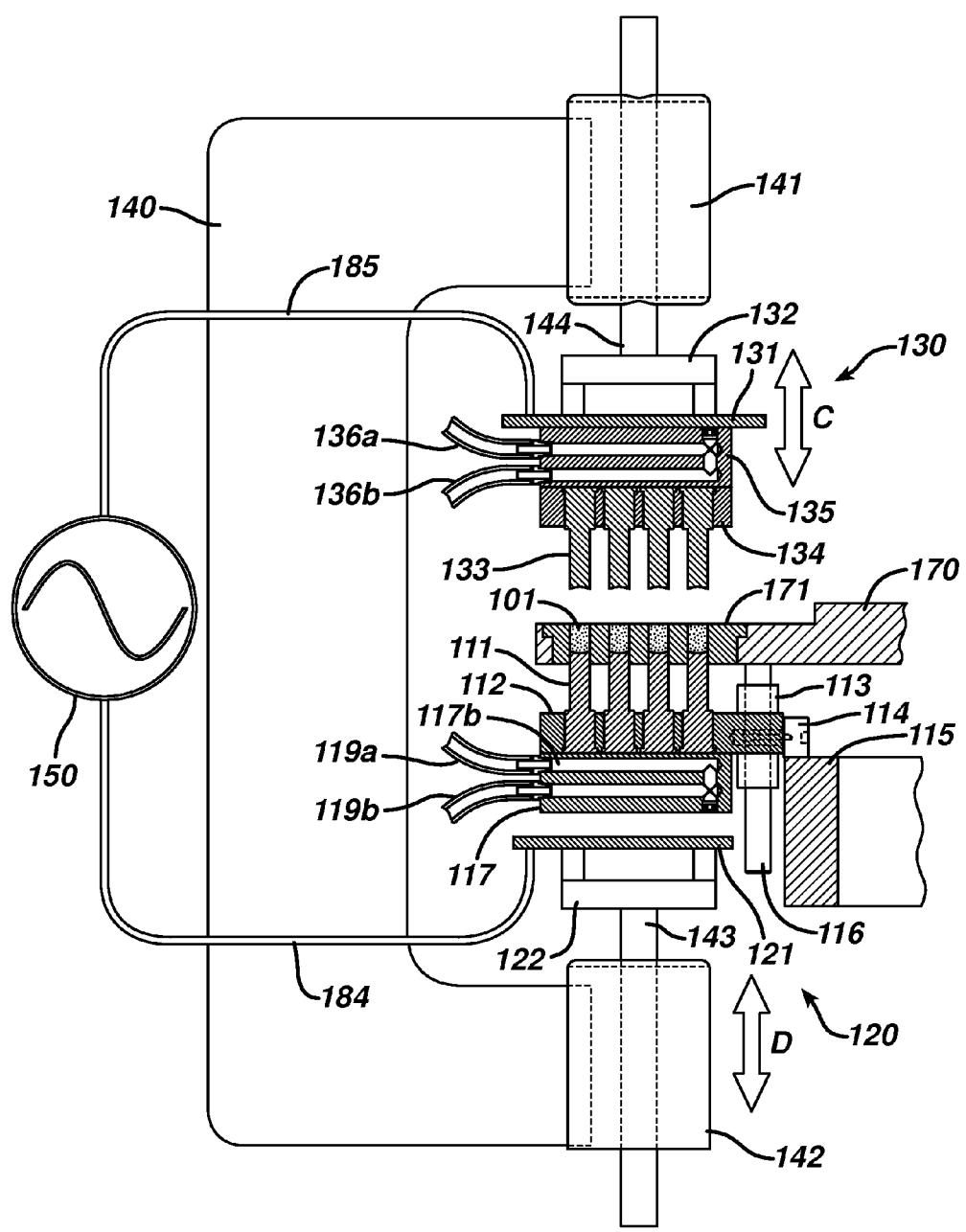
FIG. 7 is a section view through the RF station rotary indexing machine 195 prior to compacting powder blend 101.

FIG. 7 is a section view through the RF station of the apparatus. The RF generator 150 is depicted symbolically here. In one embodiment, the configuration of the RF generator 150 is a free running oscillator system. It is typically composed of a power vacuum tube (such as a triode), a DC voltage source between 1000 and 8000 volts connected across the cathode and plate (anode). A tank circuit is used to impose a sinusoidal signal upon the control grid and electrodes thereby producing the necessary frequency (typically 13.56 MHZ or 27.12 MHZ) and high voltage field. An example of such RF generator 150 is the COSMOS Model C10X16G4 (Cosmos Electronic Machine Corporation, Farmingdale, N.Y.). In another embodiment, RF energy can be provided by a 50 Ohm system composed of a waveform generator which feeds a radio frequency signal to power amplifiers which are coupled to the electrodes and the load by an impedance matching network.

In FIG. 7, a lower movable RF electrode 121 is shown, movable in direction "D". It is represented in its down position. The linear movement is generated by linear actuators which are typically devises such as air cylinders or servo motors. Two air cylinders are depicted in FIG. 7. Air cylinder bodies 141 and 142 apply pressure to guide rods 144 and 143. Moving platens 132 and 122 are connected to the guide rods and provide an electrically isolated mounting for electrode plates 131 and 121. RF generator 150 connects to the electrode plates 131 and 121 through wires 185 and 184. A movable upper RF electrode assembly 130, movable in direction "C", is shown in its up position. Upper forming tools 133, retainer plate 134, and heated block 135 are all attached to the movable RF electrode plate 131 and, consequently, move up and down with it. Powder blend 101 is within die platen 171.

Figure 8:
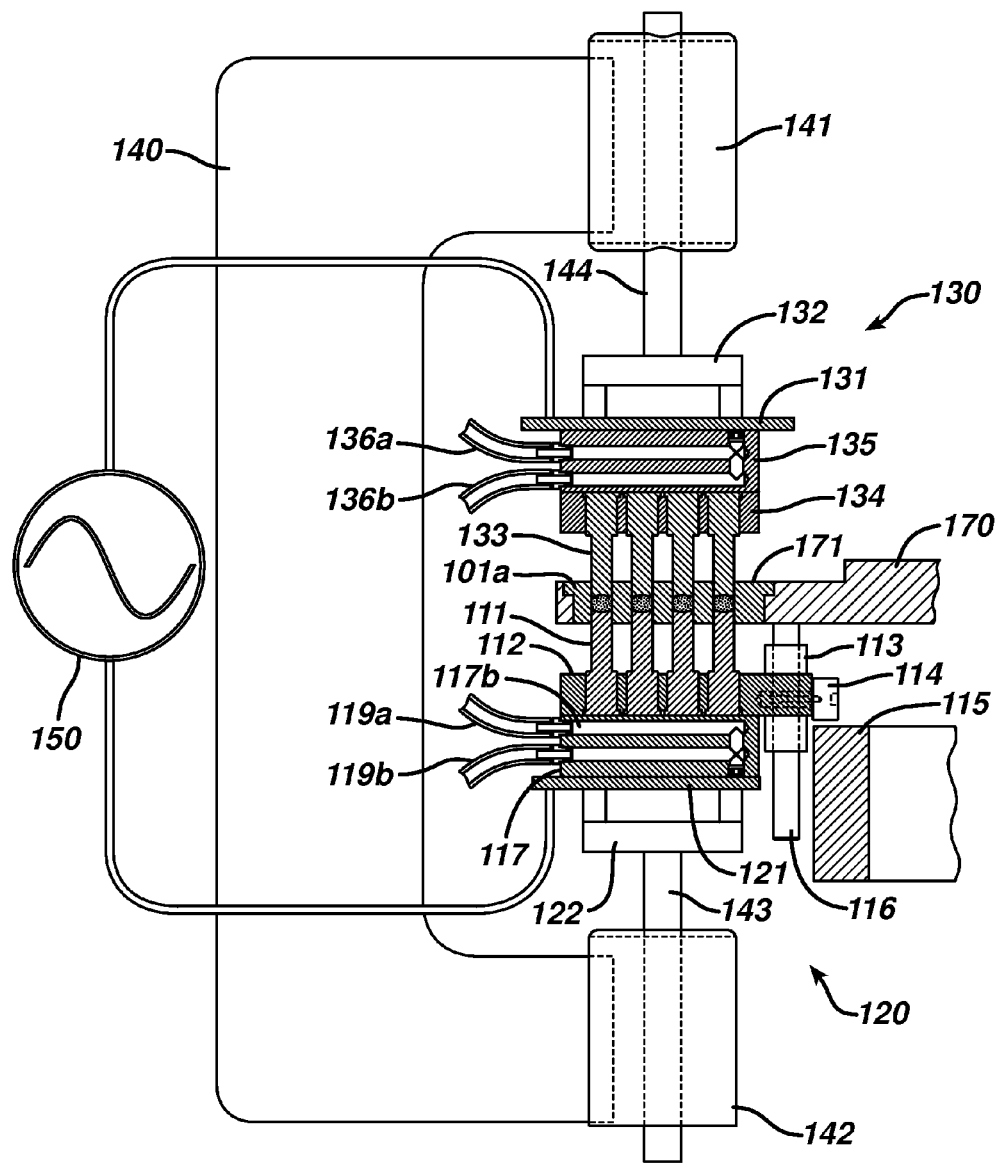

FIG. 8 is a section through the same RF station but shows the RF electrodes 131 and 121 pressing against the respective forming tool assemblies 133 and 111 to both compact and apply RF energy to powder blend 101 creating lozenge 101a. After application of the RF energy is stopped, the moveable RF electrode plates retract, and the indexing plate 170, die platen 171, and lower forming tool assembly 110 are indexed to the next station.

Figure 9:
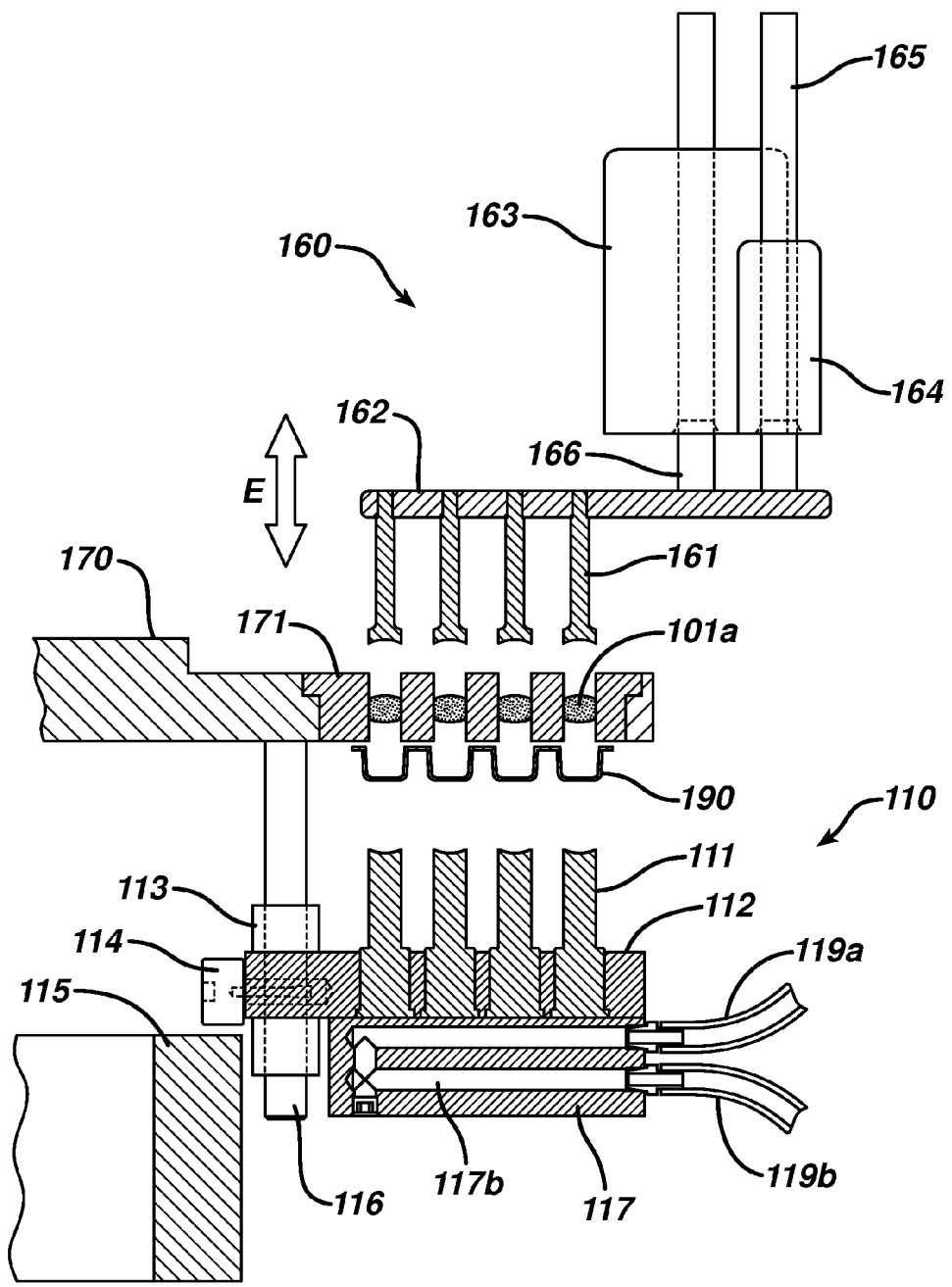
FIG. 9 is a section view through lozenge ejection station 160 before lozenges 101a have been ejected.

FIG. 9 is a section view through the lozenge ejection station 160. Ejector pins 161 are attached to movable plate 162 (movable in the "E" direction), which is actuated by actuator assembly 163 (for example, this can be a linear servo motor or air cylinder or other suitable actuator). Actuator rod 166 connects to the movable plate 162. Linear bearing 164 and guide rod 165 provide rigidity and support for the actuator plate 162 and prevent destructive side loads created by the ejection force from acting upon actuator 163. A blister package 190 is shown below die platen 171.

Figure 10:
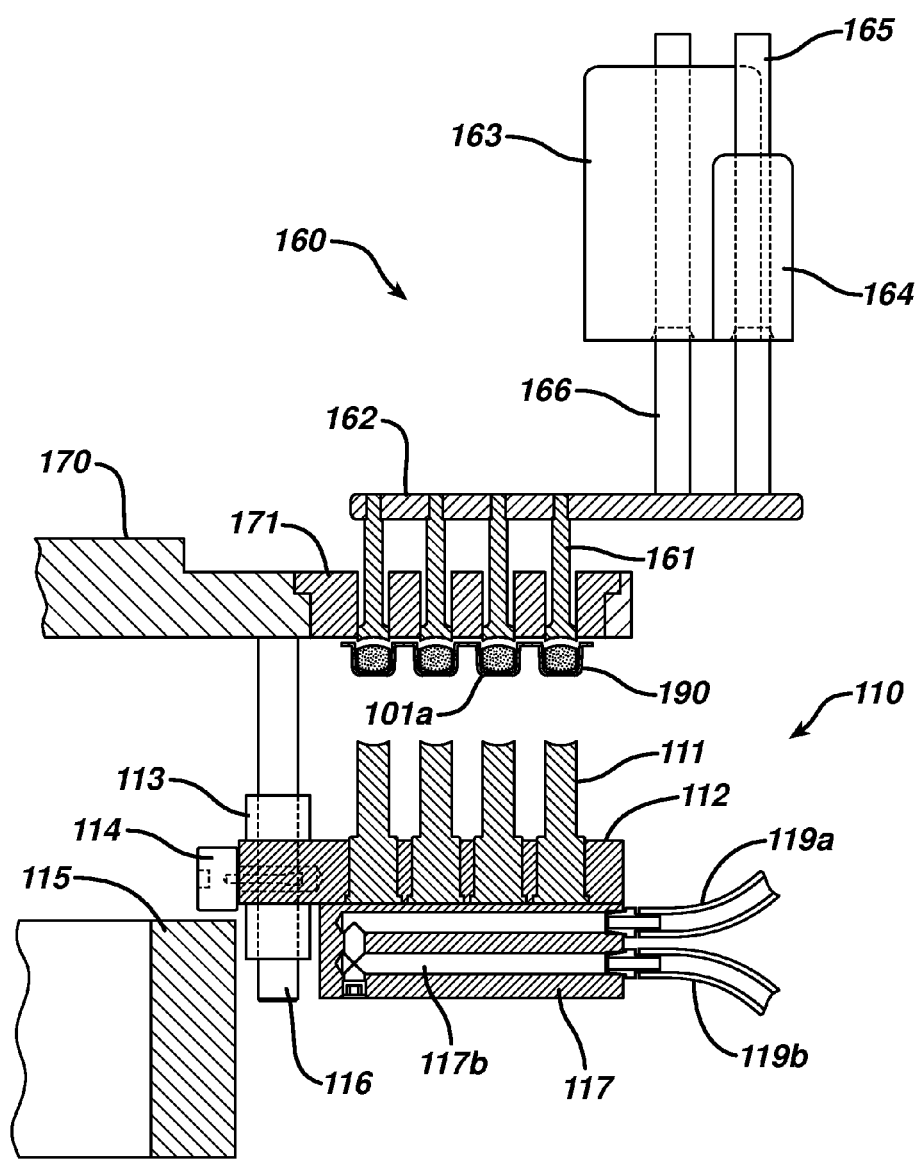
FIG. 10 is a section view through lozenge ejection station 160 after lozenges 101a have been ejected into blister 190.

FIG. 10 is a section through the same assembly after the ejector pins 161 have pushed finished lozenges 101a through the die platen 171. This direct placement of lozenge into blister helps prevent breakage that could occur while using typical means such as feeders or by dumping lozenges into transport drums.

In one embodiment, a lubricant is added to forming cavity prior to the addition of the flowable powder blend. This lubricant may be a liquid or solid. Suitable lubricants include but are not limited to solid lubricants such as magnesium stearate, starch, calcium stearate, aluminum stearate and stearic acid; or liquid lubricants such as but not limited to simethicone, lecithin, vegetable oil, olive oil, or mineral oil. In certain embodiments, the lubricant is added at a percentage by weight of the lozenge of less than 5 percent, e.g. less than 2 percent, e.g. less than 0.5 percent. In certain embodiments, the presence of a hydrophobic lubricant can disadvantageously compromise the disintegration or dissolution properties of a lozenge. In one embodiment the lozenge is substantially free of a hydrophobic lubricant. Hydrophobic lubricants include magnesium stearate, calcium stearate and aluminum stearate.

Radiofrequency Heating of Lozenge Shape to Form Lozenge

Radiofrequency heating generally refers to heating with electromagnetic field at frequencies from about 1 MHz to about 100 MHz. In one embodiment of the present invention, the RF-energy is within the range of frequencies from about 1 MHz to about 100 MHz (e.g., from about 5 MHz to 50 MHz, such as from about 10 MHz to about 30 MHz). The RF-energy is used to heat the amorphous carbohydrate polymer. The degree of compaction, the type and amount of amorphous carbohydrate polymer, and the amount of RF energy used can determine the hardness and/or type of lozenge.

RF energy generators are well known in the art. Examples of suitable RF generators include, but are not limited to, COSMOS Model C10X16G4 (Cosmos Electronic Machine Corporation, Farmingdale, N.Y.).

In one embodiment, the upper and lower forming tools serve as the electrodes (e.g., they are operably associated with the RF energy source) through which the RF energy is delivered to the lozenge shape. In one embodiment, there is direct contact between at least one RF electrode (e.g., forming tool) and the lozenge shape. In another embodiment, there is no contact between any of the RF electrode (e.g., forming tools) and the lozenge shape. In one embodiment, the RF electrodes are in direct contact with the surface of the lozenge shape when the RF energy is added. In another embodiment, the RF electrodes are not in contact (e.g., from about 1 mm to about 1 cm from the surface of the lozenge shape) during the addition of the RF energy.

In one embodiment, the RF energy is delivered while the lozenge shape is being formed. In one embodiment, the RF energy is delivered once the lozenge shape is formed. In one embodiment, the RF energy is delivered after the lozenge shape has been removed from the die.

In one embodiment, the RF energy is applied for a sufficient time to soften and melt substantially all (e.g., at least 90%, such as at least 95%, such as all) of the amorphous carbohydrate polymer within the lozenge shape. In one embodiment, the RF energy is applied for a sufficient time to soften and melt only a portion (e.g., less than 75%, such as less than 50%, such as less than 25%) of the amorphous carbohydrate polymer within the lozenge shape, for example only on a portion of the lozenge shape, such as the outside of the lozenge shape.

Figure 11A:
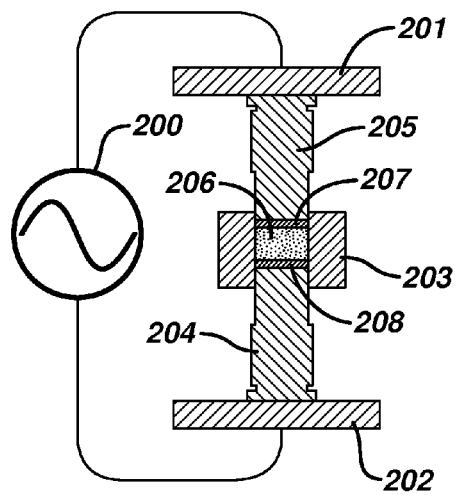
FIGS. 11A-D are cross sections of alternate embodiments of forming tools and the die platen.
Figure 11B:
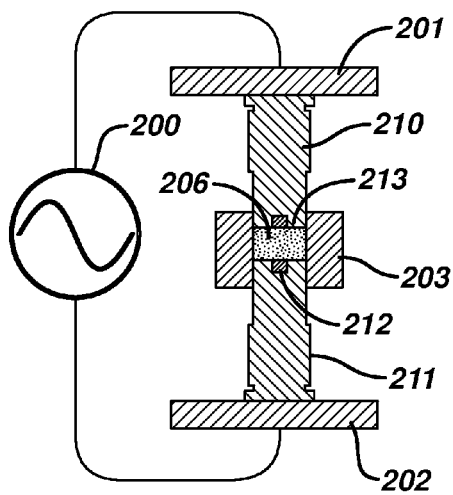
Figure 11C:
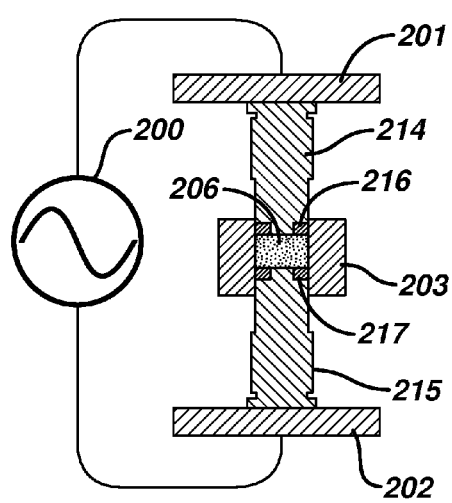
Figure 11D:
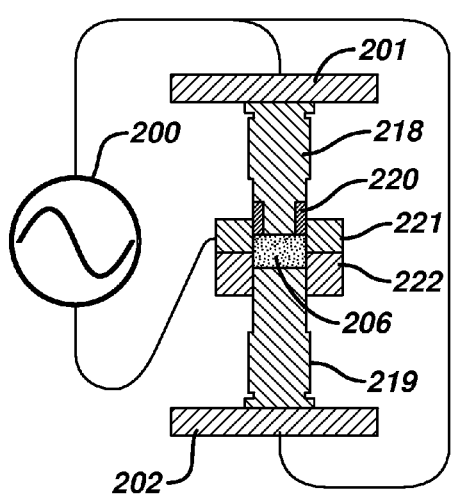

In alternate embodiments of the invention, the forming tools can be constructed to achieve localized heating effects and can also be configured to shape the electric field that is developed across the tools. FIG. 11A shows one such configuration. An RF generator 200 is connected to RF electrode plates 201 and 202. Forming tools 205 and 204 are constructed of an electrically conductive material and they have an attachment 207 and 208 which are made of electrical and RF energy insulative material such as ceramic, Teflon®, polyethylene, or high density polyethylene. Die platen 203 is also constructed of electrical and RF energy insulative material. This configuration creates greater distance between the conductive forming tools to weaken the electric field which is beneficial for producing thin lozenges without the risk of an electric arc forming which would damage the product and tooling. FIG. 11B depicts a similar configuration but with forming tools 210 and 211 that, respectively, have a recess containing insert 213 and 212 which are made of electrical and RF energy insulative material. This geometry will produce a lozenge with lesser heating in the area where the inserts 213 and 212 are located since the electric field is weaker due to the greater distance between the conductive portions of 211 and 210. FIG. 11C is similar to FIG. 11B only the geometry is reversed so the lozenge formed by this configuration will have a greater heating effect at the center since the inserts 216 and 217 are at the periphery of respective forming tools 214 and 215. FIG. 11D depicts another embodiment whereby the die platen is constructed of an electrically conductive component 221 and electrically insulating component 222, which is made of electrical and RF energy insulative material. Forming tools 219 and 218 are electrically conductive, but forming tool 218 further contains second electrically insulating component 220 around the surface of upper forming tool 218 which contact lozenge shape 206. This configuration creates an electric field and associated zones of heating that is preferential to the conductive portions of the die platen.

Figure 12A:
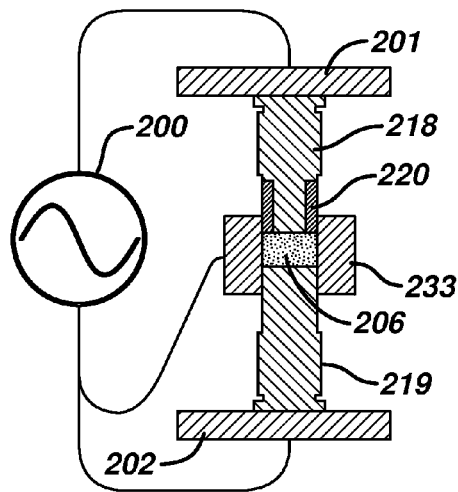
FIGS. 12A-D are cross sections of alternate embodiments of forming tools and the die platen.
Figure 12B:
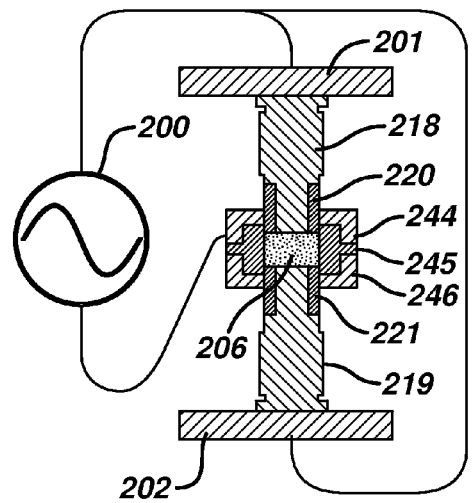
Figure 12C:
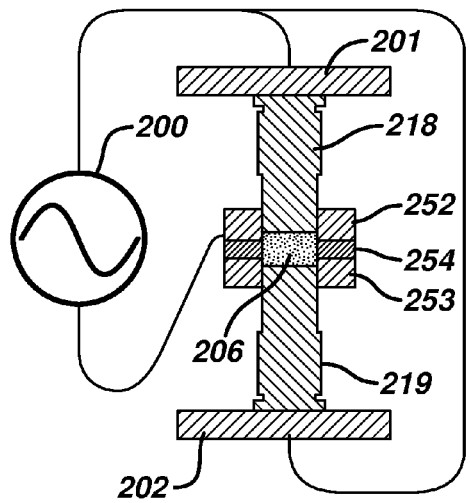
Figure 12D:
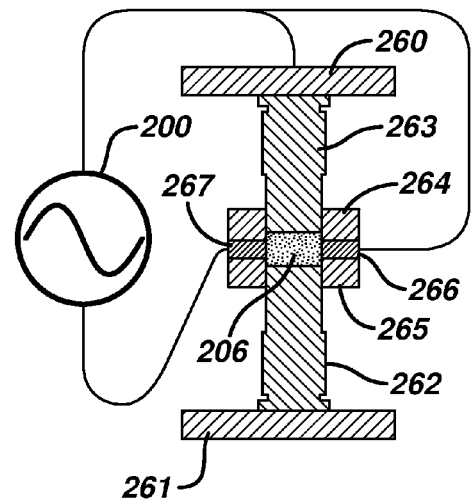

FIG. 12A is similar to FIG. 11D except the die platen 233 in this embodiment is constructed entirely of electrically conductive material. FIGS. 12B and 12C depict two embodiments where the die platen comprises a respective center portion 245 and 254 that are electrically conductive and respective outer portions 244/246 and 252/253 is are made of electrical and RF energy insulative material. FIG. 12B further includes insulating component 220 around the surface of lower forming tool 219. FIG. 12D is a further embodiment where the forming tools 263 and 262 are made of electrical and RF energy insulative material. The die platen portions 264 and 265 are made of electrical and RF energy insulative material, but there are two respective electrically conductive portions 267 and 266 which are attached to the RF generator circuit 200. In this configuration, the electric field is applied in the horizontal direction across the lozenge shape 206.

Figure 13A:
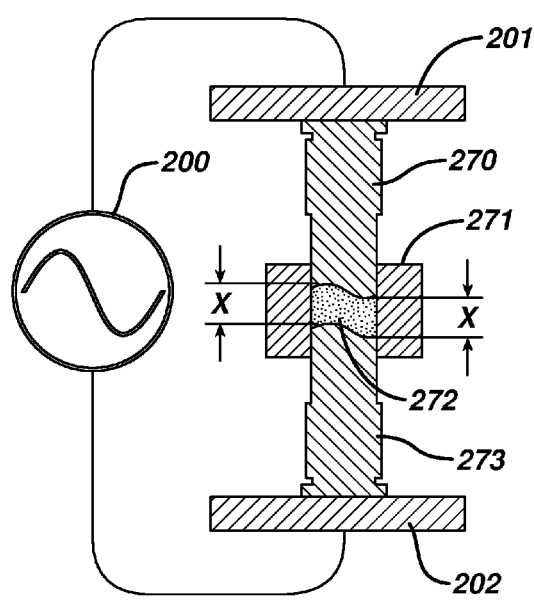
FIG. 13A is a cross section of forming tools having a wave-shaped surface.
Figure 13B:
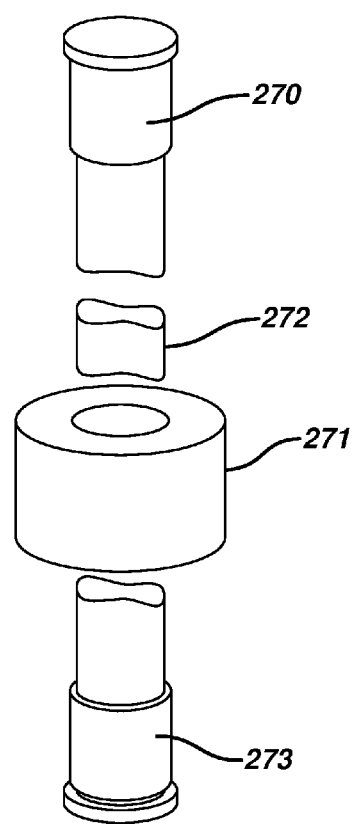
FIG. 13B is a perspective view of forming tools having a wave-shaped surface.

As described above, the distance between conductive portions of the forming tool has a strong effect on field strength and heating effect. To create a lozenge with uniform heating and texture, a forming tool that is constructed with equidistant spacing is desirable. FIGS. 13A and 13B depict such a configuration. In this embodiment, a wave-shaped forming tools 270 and 273 are shown to create a lozenge 272 within die platen 271 with a unique appearance. The profiles of the forming tool surfaces are equidistant as shown by dimension "X".

Figure 14:
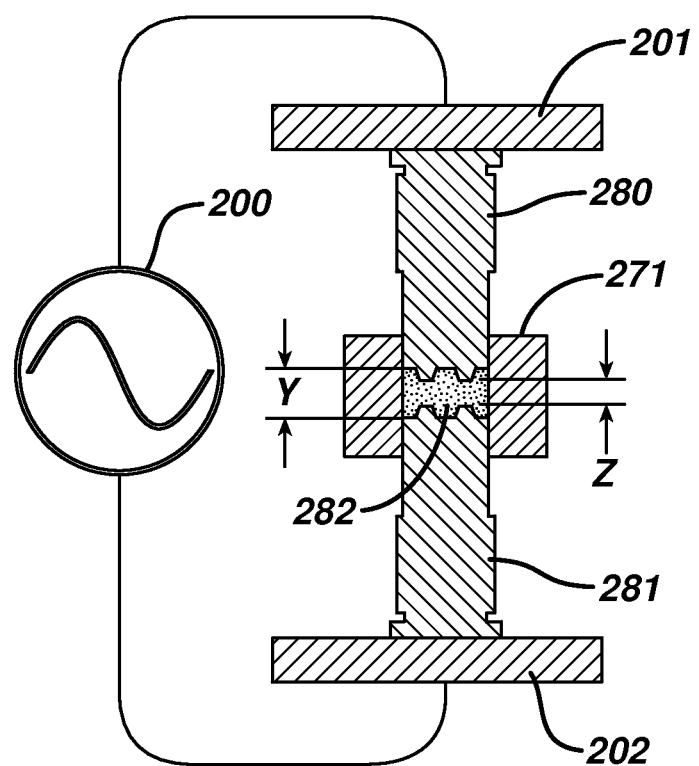
FIG. 14 is a cross section of forming tools having protrusions at the surface.

FIG. 14 is an embodiment wherein a non-uniform heating is used to manufacture lozenge 282. In this embodiment, a lozenge with hard and soft zones is created. The forming tools 280 and 281 are made with protrusions at the surface that create high field strength (resulting in greater heating) where they are closest together (shown by the dimension "Z") and weaker field strength (resulting in lesser heating) where they are further apart (shown by the dimension "Y").

In one embodiment, to help reduce sticking, the lozenge is cooled within the forming cavity to cool and/or solidify the amorphous carbohydrate polymer. The cooling can be passive cooling (e.g., at room temperature) or active cooling (e.g., coolant recirculation cooling). When coolant recirculation cooling is used, the coolant can optionally circulate through channels inside the forming tools (e.g., punches or punch platen) and/or die or die platen (e.g., as discussed above in FIGS. 6A and 6B). In one embodiment, the process uses a die platen having multiple die cavities and upper and lower punch platens having multiple upper and lower punched for simultaneous forming of a plurality of lozenges wherein the platens are actively cooled.

In one embodiment, there is a single powder blend forming the lozenge shape which is then heated with the RF energy. In another embodiment, the lozenge is formed of at least two different powder blends, at least one powder blend being RF-curable and at least one formulation being not RF-curable. When cured with RF energy, such lozenge shape develops two or more dissimilarly cured zones. In one embodiment, the outside area of the lozenge shape is cured, while the middle of the lozenge shape is not cured. By adjusting the focus of the RF heating and shape of the RF electrodes, the heat delivered to the lozenge shape can be focused to create customized softer or harder areas on the finished lozenge.

In one embodiment the RF energy is combined with a second source of heat including but not limited to infrared, induction, or convection heating. In one embodiment, the addition of the second source of heat is particularly useful with a secondary non-RF-meltable binder present in the powder blend.

Microwave Heating of Lozenge Shape to Form Lozenge

In one embodiment, microwave energy is used in place of radiofrequency energy to manufacture the lozenge. Microwave heating generally refers to heating with electromagnetic field at frequencies from about 100 MHz to about 300 GHz. In one embodiment of the present invention, the RF-energy is within the range of frequencies from about 500 MHz to about 100 GHz (e.g., from about 1 GHz to 50 GHz, such as from about 1 GHz to about 10 GHz). The microwave energy is used to heat the amorphous carbohydrate polymer. In such an embodiment, a microwave energy source and microwave electrodes are used in the machine used to manufacture the dosage form.

Inserts within Lozenge Shape

In one embodiment, an insert is incorporated into the lozenge shape before the energy is delivered. Examples include solid compressed forms or beads filled with a liquid composition.

In one embodiment, the nicotine compound and/or the pharmaceutically active agent is in the form of a gel bead, which is liquid filled or semi-solid filled. The gel bead(s) are added as a portion of the powder blend. In one embodiment, the lozenge product of this invention has the added advantage of not requiring a strong compaction step, allowing for the use of liquid or semisolid filled particles or beads which are deformable since they will not rupture following the reduced pressure compaction step. These bead walls may contain gelling substances such as: gelatin; gellan gum; xanthan gum; agar; locust bean gum; carrageenan; polymers or polysaccharides such as but not limited to sodium alginate, calcium alginate, hypromellose, hydroxypropyl cellulose and pullulan; polyethylene oxide; and starches. The bead walls may further contain a plasticizer such as glycerin, polyethylene glycol, propylene glycol, triacetin, triethyl citrate and tributyl citrate. The pharmaceutically active agent may be dissolved, suspended or dispersed in a filler material such as but not limited to high fructose corn syrup, sugars, glycerin, polyethylene glycol, propylene glycol, or oils such as but not limited to vegetable oil, olive oil, or mineral oil.

In one embodiment, the insert is substantially free of RF-absorbing ingredients, in which case application of the RF energy results in no significant heating of the insert itself. In other embodiments, the insert contains ingredients and are heated upon exposure to RF energy and, thus, such inserts can be used to melt/soften the amorphous carbohydrate polymer.

Multiple Layer Lozenges

In certain embodiments, the chewing includes at least two layers, e.g., with different types and/or concentrations of amorphous carbohydrate polymers and/or other ingredients or different concentrations of pharmaceutically active agents. Such an embodiment is shown in FIGS. 2A-2D. In one embodiment, the lozenge is a bilayer form; wherein the first layer is a lozenge form and the second layer is a orally disintegrating form. In one embodiment the first layer is a lozenge form and the second layer is a lozenge form. In one embodiment the lozenge form layer is free of a material that reacts to RF heating. In one embodiment, the lozenge form layer or the orally disintegrating form layer is first compressed as a layer, then the powder blend is added to the compressed lozenge or compressed orally disintegrating form layer and the entire form is energized utilizing the RF apparatus.

In one embodiment, the lozenge layer or the orally disintegrating form layer includes at least one material that reacts to RF heating, such as a RF heatable meltable binder or a RF heatable sugar or sugar alcohol. In one embodiment the lozenge powder blend or the orally disintegrating form blend is added to the die, and the entire form is energized utilizing the RF apparatus. In another version of this embodiment, the order of addition of the lozenge powder or orally disintegrating form blend into the RF apparatus is reversed.

In certain embodiments, the lozenge product includes at least two layers having different types and/or concentrations of ingredients (e.g., colorants or pharmaceutically active agents) within the powder blend. Such embodiments may be made by sequentially adding the powder blends that make the respective layers, forming the powders blends into the desires share of the lozenge product, and applying RF energy to the formed shape.

In another embodiment, the lozenge product further includes a second layer which is not a lozenge layer (e.g., a layer having orally disintegrating properties). In such an embodiment, upon administration of such a lozenge product having an additional orally disintegrating layer, the orally disintegrating layer quickly disintegrates in the mouth of the user, leaving the lozenge product to be sucked on by the user. In one such embodiment, the orally disintegrating layer contains one pharmaceutically active agent (e.g., an analgesic, antihistamine, decongestant, cough suppressant, or expectorant) and the lozenge product either does not contain a pharmaceutically active agent or contains a different pharmaceutically active agent (e.g., menthol).

Surface Treating of the Lozenge Product

In one embodiment, the surface of the lozenge shape and/or the lozenge product is further treated with energy (e.g., convection, infrared, or RF energy) to soften or melt the material on the surface of the lozenge product and then cooled or allowed to cool to further smooth the texture, enhance the gloss of surface of the lozenge product, limit the friability of the lozenge product, and/or provide a mark for identification. In one embodiment, the surface of the lozenge product is further exposed to infrared energy wherein the majority (at least 50 percent, such as least 90 percent, such as at least 99 percent) of the wavelength of such infrared energy is from about 0.5 to about 5 micrometers such as from about 0.8 to about 3.5 micrometers (e.g., by use of a wavelength filter). In one embodiment, the infrared energy source is a quartz lamp with a parabolic reflector (e.g., to intensify the energy) and a filter to remove unwanted frequencies. Examples of such infrared energy sources include the SPOT IR 4150 (commercially available from Research, Inc., Eden Prairie, Minn.).

Surface Gloss

In one embodiment, the lozenge product has a gloss of at least 250 gloss units, such as at least 300 gloss units, when tested using a Tri-Cor Model 805A/806H Surface Analysis System available from TriCor Systems Inc. (Elgin, Ill.) in accordance with the procedure described in "TriCor Systems WGLOSS 3.4 Model 805A/806H Surface Analysis System Reference Manual" (1996), which is incorporated by reference herein (hereinafter "gloss units").

Use of Lozenge Product

In one embodiment, the lozenge product does not contain a nicotine compound or a pharmaceutically active agent, and is used just as a candy by the user. In one embodiment, the present invention features a method of treating an ailment, the method including orally administering the above-described wherein the lozenge product includes an amount of the nicotine compound and/or pharmaceutically active agent effective to treat the ailment. Examples of such ailments include, but are not limited to, pain (such as headaches, migraines, sore throat, cramps, back aches and muscle aches), fever, inflammation, upper respiratory disorders (such as cough and congestion), infections (such as bacterial and viral infections), depression, diabetes, obesity, cardiovascular disorders (such as high cholesterol, triglycerides, and blood pressure), gastrointestinal disorders (such as nausea, diarrhea, irritable bowel syndrome and gas), sleep disorders, osteoporosis, and nicotine and/or tobacco dependence.

In this embodiment, the "unit dose" is typically accompanied by dosing directions, which instruct the patient to take an amount of the pharmaceutically active agent that may be a multiple of the unit dose depending on, e.g., the age or weight of the patient. Typically the unit dose volume will contain an amount of pharmaceutically active agent that is therapeutically effective for the smallest patient. For example, suitable unit dose volumes may include one lozenge product.

EXAMPLES

Specific embodiments of the present invention are illustrated by way of the following examples. This invention is not confined to the specific limitations set forth in these examples.

Example 1

Preparation of Placebo Lozenge Products

The lozenge products of Table 1 are prepared as follows. The sucralose, peppermint flavor and polydextrose are manually passed through a 50 mesh screen. The above mixture is placed into a plastic bottle, mixed end-over end for approximately three minutes, and then discharged. The powder blend is then individually dosed into an electrically insulative Teflon die platen having a cavity that is ½ inch in diameter. 1 mm thick Teflon discs are placed between the powder blends and the metal forming tools to help prevent arcing. The powder blend is then tamped between an upper and lower metal forming tools at about 60 psi of pressure. The forming tools, die platen and lozenge shape are then placed between the upper RF electrode and lower RF electrode powered by an RF heating unit using a COSMOS Model C10X16G4 (Cosmos Electronic Machine Corporation, Farmingdale, N.Y.) RF generator having an output of 4 KW of power, frequency of 27 MHz, and the vacuum capacitor is set at 140. The forming tools are heated with recirculating water at a temperature of 57° C. The upper RF electrode is brought into contact with the upper forming tool and the lower RF electrode is brought into contact with lower forming tool. The RF heating unit is energized for 5-15 seconds. The resulting lozenge product is then ejected from the die platen using the lower forming tool

TABLE 1

| Material | G/Batch | mg/lozenge | Weight % |
|---|---|---|---|
| Sucralose | 0.063 | 5.25 | 0.50 |
| Peppermint Flavor[1] | 0.126 | 10.50 | 1.00 |
| Polydextrose[2] | 12.411 | 1034.25 | 98.50 |
| TOTAL | 12.600 | 1050.00 | 100.0 |

[1]Commercially available from Virginia Dare in Brooklyn, NY
[2]Commercially available from Danisco in Ardsley, NY Example 2

Preparation of Coated Taste-Masked Dextromethorphan

Part A: Preparation of Layered Active Ingredient

An aqueous solution is prepared containing the following ingredients: Dextromethorphan Hydrobromide (20.0%); Polyvinyl Pyrrolidone (K29/32 grade) (1.0%); and Purified Water (79.0%). 1.96 kg of Microcrystalline cellulose (Avicel PH 200 Grade, commercially available from FMC Corporation) is charged into a fluidized bed coating apparatus (Glatt Model GPCG 5/9) fitted with a Rotor (tangential spray) Attachment. The microcrystalline cellulose is fluidized at an air flow at 36° C. and the dextromethorphan solution is sprayed at a rate of 80 g/minute, until the microcrystalline cellulose contains by weight of the layered particles approximately 40% by weight of dextromethorphan HBr.

Part B: Preparation of Coated Active Ingredient

A coating solution is prepared containing Cellulose Acetate 398-10 (commercially available from Eastman Chemical) and Eudragit E-100 (commercially available from Rohm Pharma) at a level of about 12% solids at a ratio of 80:20 Cellulose Acetate:Eudragit in acetone (total solution weight equal to 10.7 kg). A 3.0 kg portion of the particles prepared in Part A are charged into the rotor fluidized bed coating apparatus (Glatt Model GPCG 5/9). The drug-layered particles are fluidized at 36° C. and the polymer solution is sprayed on at a rate of 40 g/minute until the drug particles contain approximately 20% by weight of the polymer coating.

Example 3

Preparation of Lozenge Products Containing Coated Dextromethorphan

The lozenges of Table 2 are prepared as follows. The sucralose, peppermint flavor and polydextrose are manually passed through a 50 mesh screen. The above mixture is combined with the coated dextromethorphan from Example 2 and placed in a plastic bottle, mixed end-over end for approximately three minutes, and then discharged. The powder blend is then placed into the forming cavity, tamped, and activated with RF energy as described in Example 1 to form the lozenge and subsequently removed from the die platen.

TABLE 2

| Material | G/Batch | mg/lozenge | Weight % |
|---|---|---|---|
| Sucralose | 0.46 | 5.25 | 0.46 |
| Coated Dextromethorphan (32%)* | 7.93 | 90.45 | 7.93 |
| Peppermint Flavor[1] | 0.92 | 10.50 | 0.92 |
| Polydextrose[2] | 90.69 | 1034.25 | 90.69 |
| TOTAL | 100.0 | 1140.45 | 100.0 |

[1]Commercially available from Virginia Dare in Brooklyn, NY
[2]Commercially available from Danisco in Ardsley, NY

Example 4

Preparation of Lozenge Products Containing Menthol

The lozenges of Table 3 are prepared as follows. The sucralose, peppermint flavor and polydextrose are manually passed through a 50 mesh screen. The above mixture is combined with the menthol and placed in a plastic bottle, mixed end-over end for approximately three minutes, and then discharged. The powder blend is then placed into the forming cavity, tamped, and activated with RF energy as described in Example 1 to form the lozenge and subsequently removed from the die platen.

TABLE 3

| Material | G/Batch | mg/lozenge | Weight % |
|---|---|---|---|
| Sucralose | 0.49 | 5.25 | 0.49 |
| Menthol | 1.13 | 12.00 | 1.13 |
| Peppermint Flavor[1] | 0.99 | 10.50 | 0.99 |
| Polydextrose[2] | 97.39 | 1034.25 | 97.39 |
| TOTAL | 100.0 | 1062.00 | 100.0 |

[1]Commercially available from Virginia Dare in Brooklyn, NY
[2]Commercially available from Danisco in Ardsley, NY

Example 5

Preparation of Lozenge Products Containing Nicotine Bitartrate Dihydrate

The lozenges of Table 4 are prepared as follows. The sucralose, peppermint flavor and polydextrose are manually passed through a 50 mesh screen. The above mixture is combined with the nicotine bitartrate dihydrate and L-Arginine and placed in a plastic bottle, mixed end-over end for approximately three minutes, and then discharged. The powder blend is then placed into the forming cavity, tamped, and activated with RF energy as described in Example 1 to form the lozenge and subsequently removed from the die platen.

TABLE 4

| Material | G/Batch | mg/lozenge | Weight % |
|---|---|---|---|
| Sucralose | 0.49 | 5.25 | 0.49 |
| Nicotine Bitartrate Dihydrate (32.55% Nicotine) | 0.29 | 3.08* | 0.29 |
| L-Arginine | 2.01 | 21.6 | 2.01 |
| Peppermint Flavor[1] | 0.98 | 10.50 | 0.98 |
| Polydextrose[2] | 96.24 | 1034.25 | 96.24 |
| TOTAL | 100.0 | 1074.68 | 100.0 |

[1]Commercially available from Virginia Dare in Brooklyn, NY
[2]Commercially available from Danisco in Ardsley, NY
*Equivalent to a 1.0 mg Dose of Nicotine

Example 6

Preparation of Lozenge Products Containing Nicotine Resin Complex

The lozenges of Table 5 are prepared as follows. The sucralose, peppermint flavor and polydextrose are manually passed through a 50 mesh screen. The above mixture is combined with the nicotine resin complex and the trometamol and placed in a plastic bottle, mixed end-over end for approximately three minutes, and then discharged. The powder blend is then placed into the forming cavity, tamped, and activated with RF energy as described in Example 1 to form the lozenge and subsequently removed from the die platen.

TABLE 5

| Material | G/Batch | mg/lozenge | Weight % |
|---|---|---|---|
| Sucralose | 0.50 | 5.25 | 0.50 |
| Nicotine Resin Complex (20% Nicotine) | 0.24 | 2.50* | 0.24 |
| Trometamol | 0.71 | 7.5 | 0.71 |
| Peppermint Flavor[1] | 0.99 | 10.50 | 0.99 |
| Polydextrose[2] | 97.57 | 1034.25 | 97.57 |
| TOTAL | 100.0 | 1060.00 | 100.0 |

[1]Commercially available from Virginia Dare in Brooklyn, NY
[2]Commercially available from Danisco in Ardsley, NY
*Equivalent to a 0.5 mg Dose of Nicotine

Example 7

Manufacture of Bi-Layer Lozenge Product Orally Disintegrating Layer

Part A: Preparation of Powder Blend Containing Loratadine

The loratadine powder blend for an orally disintegrating layer, containing the ingredients of Table 6, is manufactured as follows:

TABLE 6

| Ingredient | G/Batch | Mg/Layer |
|---|---|---|
| Dextrose Monohydrate | 45.18 | 120 |
| Loratadine | 3.765 | 10 |
| Polyethylene Glycol 4000 | 24.475 | 65 |
| Maltodextrin | 15.062 | 40 |
| Red Colorant | 0.028 | 0.075 |
| Simethicone DC100 | 5.648 | 15 |
| Sucralose USP | 1.13 | 3 |

TABLE 6-continued

| Ingredient | G/Batch | Mg/Layer |
|---|---|---|
| Polyethylene Oxide | 1.883 | 5 |
| Mint Flavor | 2.824 | 7.5 |
| Total | 100 | 265.58 |

First, the sucralose, colorant, and flavor are placed together into a 500 cc sealable plastic bottle. The mixture is then blended end-over-end manually for approximately 2 minutes. The resulting mixture, the dextrose monohydrate, loratadine, and the polyethylene oxide are then added to another 500 cc sealable plastic bottle and mixed end-over-end manually for approximately 5 minutes. The resulting mixture is then added to a planetary bowl mixer, and the simethicone DC 100 is added and mixed for approximately 3 minutes. Lastly, the polyethylene glycol 4000 and the maltodextrin is added to the mixture and mixed for approximately 3 minutes.

Part B: Manufacture of Orally Disintegrating and Lozenge Bi-Layer Dosage Form

A 1062 mg 265.58 mg portion of the powder blend from Example 4 is placed into a non-conductive die platen, approximately ½ inch in diameter. The powder blend is then placed into the forming cavity, tamped, and activated with RF energy as described in Example 1 (but the RF heating unit is energized for 15 seconds). The upper forming tool is then removed and 265.58 mg of the blend from Example 7(a) containing loratadine is added. The forming tool is reinserted into the forming cavity and the RF heating unit is then energized for an additional 2 seconds. The resulting final bilayer dosage form is then ejected from the die using the lower tool.

Example 8

Nicotine Lozenge Prepared using Hydrogen Starch Hydrolysate

The lozenges of Table 7 are prepared as follows. The sucralose, peppermint flavor and hydrogenated starch hydrolysate are manually passed through a 50 mesh screen. The above mixture is then combined with the nicotine resin complex, and the remaining materials and placed in a plastic bottle, mixed end-over end for approximately three minutes, and then discharged. The powder blend is then placed into the forming cavity, tamped, and activated with RF energy as described in Example 1 to form the lozenge and subsequently removed from the die platen.

TABLE 7

| Material | G/Batch | mg/lozenge | Weight % |
|---|---|---|---|
| Hydrogenated Starch Hydrolysate[1] | 190.90 | 954.50 | 94.45 |
| Sodium Bicarbonate USP | 0.50 | 2.50 | 0.25 |
| Sodium Carbonate, Anhydrous | 1.00 | 5.00 | 0.50 |
| Nicotine Resin Complex (20% Nicotine) | 2.20 | 11.00* | 1.10 |
| Acesulfame Potassium E950 Type D[3] | 0.40 | 2.00 | 0.20 |
| Peppermint Flavor[1] | 4.00 | 20.00 | 2.00 |
| Micronized Sucralose | 1.00 | 5.00 | 0.50 |
| TOTAL | 200.0 | 1060.00 | 100.0 |

[1]Commercially available as Stabilite PD30 Polyglycitol (HSH), commercially available from the Corn Products Company, in Westchester, IL, USA
[2]Commercially available from Virginia Dare in Brooklyn, NY
[3]Commercially available from the Nutrinova Company in Frankfurt, Germany
*Equivalent to a 2 mg dose of Nicotine It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A process for making a lozenge, said method comprising the steps of forming a powder blend comprising an amorphous carbohydrate polymer into the desired shape of said lozenge in a die of an apparatus and applying RF energy from said apparatus to said shape within said die for a sufficient period of time to soften or melt said amorphous carbohydrate polymer to fuse said powder blend into said lozenge; wherein said process comprises the steps of:
   (i) introducing said powder blend into a forming cavity within said die platen;
   (ii) compacting said powder blend by introducing at least one forming tool into said die platen with sufficient force such that the shape of the lozenge is formed;
   (iii) applying said radiofrequency energy to said shape within said forming cavity to form said lozenge wherein said at least one said forming tool or said die platen emits said radiofrequency energy to said lozenge shape; and
   (iv) removing said lozenge from said forming cavity.

2. The process of claim 1, wherein said RF energy has a frequency of from about 1 MHz to 100 MHz.

3. The process of claim 1, wherein said amorphous carbohydrate polymer is selected from the group consisting of polydextrose, fructo-oligosaccharide, galacto-oligosaccharide, malto-oligosaccharide, isolmalto-oligosaccharide, and hydrogenated starch hydrolysate.

4. The process of claim 1, wherein said powder blend comprises nicotine or a salt thereof.

5. The process of claim 1, wherein said powder blend comprises a pharmaceutically active agent.

6. The process of claim 1, wherein said powder blend comprises phenylephrine, dextromethorphan, pseudoephedrine, chlorpheniramine, methocarbomal, chlophedianol, ascorbic acid, menthol, pectin, dyclonine, and benzocaine, and pharmaceutically acceptable salts thereof.

7. The process of claim 1, wherein said powder blend comprises from about 50 to about 99.9 percent, by weight, of said amorphous carbohydrate polymer.

8. The process of claim 1, wherein the lozenge has a gloss of at least 250 gloss units.

9. The process of claim 1, wherein said process further comprises adding a second powder blend to said die wherein said second powder blend is different from the first powder blend.

10. The process of claim 1, wherein said process further comprises the step of cooling said lozenge in said die prior to removing said lozenge from said die.

11. The process of claim 1, wherein said at least one said forming tool emits said radiofrequency energy to said shape.

12. The process of claim 1, wherein the die platen emits said radiofrequency energy to said shape.

13. The process of claim 1, wherein said powder blend is compacted using an upper forming tool and a lower forming tool, and at least one of said upper forming tool or lower forming tool emits said radiofrequency energy to said shape.

14. The process of claim 1, wherein said process further comprises adding a second powder blend to said forming cavity prior to said step of applying radiofrequency energy to shape, wherein said second powder blend is different from said powder blend.

15. The process of claim 1, wherein the surface of said lozenge is further exposed to infrared energy wherein the majority of the wavelength of said infrared energy from about 0.5 to about 5 micrometers.

16. A lozenge manufactured according to the process of claim 1.

17. A lozenge of claim 16, wherein said lozenge comprises nicotine or a salt thereof.

18. A method of treating nicotine or tobacco dependence, said method comprising administering to a patient in need to such treatment the lozenge of claim 17.

19. The process of claim 2, wherein said powder blend comprises from about 50 to about 99.9 percent, by weight, of said amorphous carbohydrate polymer.

20. The process of claim 3, wherein said powder blend comprises from about 50 to about 99.9 percent, by weight, of said amorphous carbohydrate polymer.

21. The process of claim 5, wherein said powder blend comprises from about 50 to about 99.9 percent, by weight, of said amorphous carbohydrate polymer.

22. The process of claim 11, wherein said powder blend comprises from about 50 to about 99.9 percent, by weight, of said amorphous carbohydrate polymer.

23. The process of claim 13, wherein said powder blend comprises from about 50 to about 99.9 percent, by weight, of said amorphous carbohydrate polymer.

24. The process of claim 3, wherein said at least one said forming tool emits said radiofrequency energy to said shape.

25. The process of claim 5, wherein said at least one said forming tool emits said radiofrequency energy to said shape.

26. The process of claim 7, wherein said at least one said forming tool emits said radiofrequency energy to said shape.

27. The process of claim 19, wherein said at least one said forming tool emits said radiofrequency energy to said shape.

28. The process of claim 20, wherein said at least one said forming tool emits said radiofrequency energy to said shape.

29. The process of claim 21, wherein said at least one said forming tool emits said radiofrequency energy to said shape.

* * * * *